US012807869B2

(12) United States Patent
Rózsa et al.

(10) Patent No.: US 12,807,869 B2
(45) Date of Patent: Nov. 24, 2026

(54) RED FLUORESCENT SENSOR COMPOUNDS FOR THE DETECTION OF METAL IONS

(71) Applicant: FEMTONICS KFT., Budapest (HU)

(72) Inventors: J. Balázs Rózsa, Budapest (HU); Gergely Katona, Budapest (HU); Zoltán Mucsi, Budapest (HU); Ervin Kovács, Budapest (HU); Attila Csomos, Budapest (HU)

(73) Assignee: FEMTONICS KFT., Budapest (HU)

( * ) Notice: Subject to any disclaimer, the term of this patent is extended or adjusted under 35 U.S.C. 154(b) by 764 days.

(21) Appl. No.: 18/265,207

(22) PCT Filed: Dec. 4, 2021

(86) PCT No.: PCT/HU2021/050066

§ 371 (c)(1),
(2) Date: Jun. 2, 2023

(87) PCT Pub. No.: WO2022/118054

PCT Pub. Date: Jun. 9, 2022

(65) Prior Publication Data

US 2024/0010913 A1 Jan. 11, 2024

(30) Foreign Application Priority Data

Dec. 4, 2020 (HU) .................................... P2000416

(51) Int. Cl.

| | |
|---|---|
| ***C09K 11/06*** | (2006.01) |
| ***C07D 401/06*** | (2006.01) |
| ***C07D 471/14*** | (2006.01) |
| ***C07F 3/06*** | (2006.01) |
| ***G01N 21/64*** | (2006.01) |
| ***G01N 33/84*** | (2006.01) |

(52) U.S. Cl.

CPC ............ *C09K 11/06* (2013.01); *C07D 401/06* (2013.01); *C07D 471/14* (2013.01); *C07F 3/06* (2013.01); *G01N 33/84* (2013.01); *C09K 2211/1029* (2013.01); *C09K 2211/1044* (2013.01); *C09K 2211/188* (2013.01); *G01N 2021/6439* (2013.01)

(58) Field of Classification Search

CPC .................................................... C07D 471/14

See application file for complete search history.

(56) References Cited

FOREIGN PATENT DOCUMENTS

EP 818512 A1 1/1998

OTHER PUBLICATIONS

Li Yang et al: "An OFF-ON fluorescent probe for Zn2+ based on a GFP-inspired imidazolone derivative attached to a 1,10-phenanthroline moiety", Chemical Communications, vol. 47, No. 15, Jan. 1, 2011 (Jan. 1, 2011), UK, pp. 4361, XP055908383, ISSN: 1359-7345, DOI: 10.1039/c1cc10210a.

(Continued)

*Primary Examiner* — Peter F Godenschwager

(74) *Attorney, Agent, or Firm* — Csaba Henter; MILLEN, WHITE, ZELANO & BRANIGAN, P.C.

(57) ABSTRACT

The present invention relates to novel red fluorescent sensors for detecting metal ions, preferably zinc ions, which have a chemical structure corresponding to a compound of general formula I. These sensors are very useful for determining the concentration and distribution of zinc in living cells or tissues, preferably in a laser microscopic assay.

17 Claims, 9 Drawing Sheets

28

(56) References Cited

OTHER PUBLICATIONS

Li Yang et al: "An OFF-ON fluorescent probe for Zn 2+ based on a GFP-inspired imidazolone derivative attached to a 1,10-Phenanthroline moiety-Supplementary Material", Jan. 1, 2011 (Jan. 1, 2011), pp. 1-14, XP055908761, Retrieved from the Internet <URL:https://www.rsc.org/suppdata/cc/c1/c1cc10210a/c1cc10210a.pdf> [retrieved on Apr. 4, 2022].
Hu Xuan et al: "Construction of a luminescent sensor based on a lanthanide complex for the highly efficient detection of methyl parathion", RSC Advances, vol. 9, No. 23, Apr. 29, 2019 (Apr. 29, 2019), GB, pp. 13048-13053, XP055908574, ISSN: 2046-2069, DOI: 10.1039/C9RA01748H.
Walker Christopher L et al: "Fluorescence imaging using synthetic GFP chromophores", Current Opinion in Chemical Biology, vol. 27, Aug. 1, 2015 (Aug. 1, 2015), GB, pp. 64-74, XP055909231, ISSN: 1367-5931, DOI: 10.1016/j.cbpa.2015.06.002.
Csomos Attila: "Design, Synthesis and Analysis of Novel Fluorescent Probes for Two- Photon Zinc Imaging", Dec. 5, 2020 (Dec. 5, 2020), pp. 1-89, XP055908927, Retrieved from the Internet <URL:http://kemiatdk.elte.hu/downloads/konf2020/csomos_attila_dolgozat2020.pdf> [retrieved on Apr. 5, 2022].
International search report PCT/HU2021/050066 dated Apr. 25, 2022 (pp. 1-5) and written opinion (pp. 1-17).
Gutierrez et al: "Highly Fluorescent Green Fluorescent Protein Chromophore Analogues Made by Decorating the Imidazolone Ring"; Chemistry—A European Journal vol. 21, Issue 51 pp. 18758-18763 ; https://doi.org/10.1002/chem.201502929.
Hungarian Patent Office Examination report HU P20000416/18 dated Apr. 14, 2023 (pp. 1-5) .
Qi-Hua You et al: "A quinolinyl antipyrine based flourescence sensor for Zn2+ and its application in bioimaging" RSC Advances Dec. 2012, 11078-11083.
Search report in Hungarian application Hu P20000416/18 dated Mar. 24, 2022 (pp. 1-6).
Attila Jancso et al: "Synthesis and spectroscopic characterization of novel GFP chromophore analogues based on aminoimidazolone derivatives" Spectrochimica Acta, Part A: ; Molecular and Biomolecular Spectr vol. 218 Jul. 5, 2019 pp. 161-170; https://doi.org/10.1016/j.saa.2019.03.111.

28

32

33

31

30

34

35

30 Free, Zn2+ Ca2 Mg2+ Na+ K+ Fe3+ Cu2+ Sn2+ Cd2+ Pb2+

29 Free, Zn2+ Ca2 Mg2+ Na+ K+ Fe3+ Cu2+ Sn2+ Cd2+ Pb2+

31 Free, Zn2+ Ca2 Mg2+ Na+ K+ Fe3+ Cu2+ Sn2+ Cd2+ Pb2+

33 Free, Zn2+ Ca2 Mg2+ Na+ K+ Fe3+ Cu2+ Sn2+ Cd2+ Pb2+

RED FLUORESCENT SENSOR COMPOUNDS FOR THE DETECTION OF METAL IONS

Present invention relates: New red fluorescent sensor compounds for the detection of metal ion, preferably Zinc ion having a general formula

I

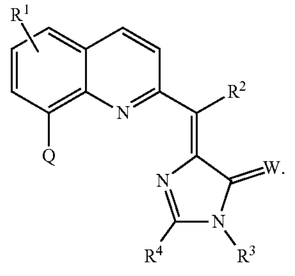

which compounds have very advantageous properties for the use for the microscopic imaging the concentration of Zn2+ in solution, even living cells, cell cultures, tissues by using laser microscopy technique.

TECHNICAL BACKGROUND

The measurement of zinc concentration in living organisms, tissues, cells, cell cultures is important since it was proven in 1961 that zinc is an essential element in living organisms by taking part in a surprising number of processes, according to document of Jancsó A. at al, Spectrochim. Acta Part A Mol. Biomol. Spectrosc. 2019, 218, 161-170/doc. 10/. In general, zinc is a redox-inert element in the body always being present in +2 oxidation state, mostly in colourless coordination complexes with coordination numbers of 2, 4 and 6 according to document of Johnson, A. D. at al. Chemosensors 2019, 7 (2) /doc. 6/. According to the literature, the total zinc content of a human body is cca. 2-3 g, while the concentration values in different parts of the body are highly varied.

Since the concentration of the analyte is one of the most important factors to consider, when designing sensor molecules, it is principal to find out what concentration ranges can be expected during the application. However, measurement of the concentration of $Zn^{2+}$ is problematic, since most of the ions are bounded to proteins and hidden in compartments of cells according to article of Maret, W., Adv. Nutr. 2013, 4 (1), 82-91. /doc. 5/. This is the reason, that even conservative estimates suggest, that more than 17-25% of the world population is zinc-deficient to some extent, altering their vital functions according to document /5/ above, Mayor-Ibarguren, A. at al, Front. Immunol. 2020, 11 (July), 1-8. /doc. 12/ and Maret, W. at. al Trace Elem. Med. Biol. 2006, 20 (1), 3-18. /doc. 13/.

Although different $Zn^{2+}$ level values are reported in the human blood plasma, a concentration range of 10-25 μM can be accepted as described in documents /6, 12 and 13/ above, “Free”, unbound cellular $Zn^{2+}$ levels are also variable and multiple values were reported. The reported concentration ranges from tens of picomoles per liter to nanomolar and micromolar concentrations. Higher concentrations covering mM ranges are localized in different parts of the body, such as breasts, prostate, pancreas, CNS. Generally, the free ion content is important for sensor molecules, as classically ionophores mainly bind to free, unbound ions. Consequently, these species are the ones, that can be indicated by fluorescent probes. However, the situation in case of $Zn^{2+}$ is more complicated. While $Zn^{2+}$ is rarely present in free form, the protein bounded $Zn^{2+}$ can be tightly bounded ($pK_d$>11), moderately ($pK_d$=~7-9) and loosely bounded ($pK_d$<~7) according to the document /6/ above. Since the binding of the ions follows an equilibrium, an ionophore probe could be able to shift the equilibrium and release bound ions from proteins only to connect to them according to the document of Palmer, A. E. at. al.; Encycl. Inorg. Bioinorg. Chem. 2004, No. Ii, 1-14. /16/. Moreover, if a protein does not bind to all the coordinative sites of $Zn^{2+}$ and the ion is close to the surface of the complex, chelator fluorescent probes often binds to the residual coordinative sites, this way turning on. The distribution of $Zn^{2+}$ in cells is visualized on FIG. 1.

In conclusion, fluorescent sensors for $Zn^{2+}$ works in concentrations ranging from nM to mM, depending on its application. The complexity of $Zn^{2+}$ distribution requires a wide range of different probes for different purposes and expanding the available set of fluorescent probes with completely new scaffolds could help broadening the possible investigations through microscopy, which could lead to answering new scientific questions.

In general, $Zn^{2+}$ and its deficiency are also related to multiple diseases. It was documented by Doboszewska, U. at. al.; Br. J. Pharmacol. 2020, 177 (21), 4887-4898/3/ and Shittu, M. O. et. al.; Infez. Med. 2020, 28 (2), 192-197. /9/, that zinc has anti- and proinflammatory properties at the same time, antiviral properties and plays role in general in immunity, even though the mechanism of these effects is debated in the scientific milieu. Furthermore, many signs show, that $Zn^{2+}$ plays significant role in COVID-19 discussed in the documents /3,9,12 above and an article of Hecel, A. et. al.; A. 2020, No. II, 1-29. /8/. There has been several news, rumours and tips, that taking zinc diet supplements help avoiding a serious COVID-19 disease. Besides this, originating from its role in signaling, zinc is an important element of neurological diseases, such as Alzheimer’s disease, neuronal injury and amyotrophic lateral sclerosis according to documents /3,6,8,9/, and /12/ above and documents Chang, C. J.; at. al. Zinc Metalloneurochemistry: Physiology, Pathology, and Probes; 2006; Vol. 1. /17/, Frederickson, C. J.; at. al. Nat. Rev. Neurosci. 2005, 6 (6), 449-462/19/ and Valeur, B.; at. al. Coord. Chem. Rev. 2000, 205 (1), 3-40 /20/. The link between $Zn^{2+}$ and the mentioned diseases also indicates the importance of our field of the present invention.

As mentioned before, $Zn^{2+}$ has a role in immunity in general, and it was also suggested to limit the cytokine storm happening according to document Skalny, A. V.; at. al. A. Int. J. Mol. Med. 2020, 46 (1), 17-26 /21/ in severe COVID-19 patients due to its anti-inflammatory properties. Higher ratio of zinc deficiency in elderly people was also connected to the fact, that the death ratio of the disease increases significantly with age. Taking $Zn^{2+}$ combined with a moderately strong zinc-ionophore was shown to increase cellular concentrations of the metal. The ionophore binds to the $Zn^{2+}$ in the extracellular region, where the $Zn^{2+}$ concentration is larger, then by crossing the cell membrane, it transports the ions into cells, where the complex dissociates due to the low local $Zn^{2+}$ concentration. In the case of SARSCoV1, the RNA dependent RNA polymerase (further RdRp) of the virus was inhibited by $Zn^{2+}$. It was suggested, that the RdRp may be inhibited in the case of SARSCoV2 as well by $Zn^{2+}$, consequently, multiple drugs, with zinc-ionophore properties are currently being tested with and without supplementary zinc intake in clinical tests according to documents /3,8,9,12,21/. Just to mention the most important ones, this is one of the suspected mechanisms of drugs known as chloroquine (1a), hydroxychloroquine (1b) (see FIG. 2.), which are also zinc-ionophores. In addition to these, a numerous amount of zinc-ionophores are known as antiviral agents according to document /8/.

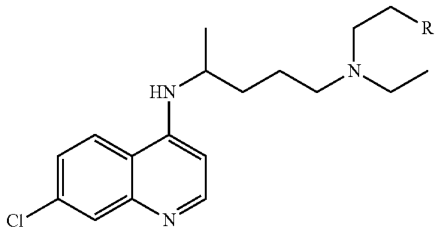

1a: R = H chloroquine
1b: R = OH hydroxychloroquine

FIG. 1. Structure of zinc-ionophores under clinical trial against COVID-19. Violet colour marks heteroatoms suggested to bind zinc.

Angiotensin-converting enzyme 2 (further ACE2), which is the key entry point into cells for SARS-CoV-2 is also one of the many zinc-proteins and indirect evidence suggests, that $Zn^{2+}$ may decrease its activity. Zinc-ionophores were shown to reduce the glycosylation of ACE2 receptor, and as a result, lower its affinity towards the viral spike proteins, therefore inhibiting viral access into the cells according to document /21/ above.

Another possible target of zinc-ionophores may be the papain-like protease (further $PL^{pro}$) enzyme of SARS-CoV-2, which is stabilized by zinc fingers. It was suggested, that removing zinc with ionophores from this enzyme would destabilize it, therefore rendering it useless for viral reproduction, while the liberated zinc could inhibit the RdRp further inhibiting the reproduction of the virus.

Besides these, a multitude of relations were hypothesized in the scientific literature between zinc and the COVID-19. More sources include links between zinc and influenza, pneumonia, other infections and multiple cellular biological processes. Due to our opinion mentioned discoveries are the most important ones, and the most plausible ones representing the relation between zinc and COVID-19. All the mentioned findings need to be treated with caution as presumptions, and not as proven facts. More research is needed in the field to clarify relations and reach consensus. Nonetheless, all these results confirm, that zinc plays important roles in this viral infection, accordingly, it should be taken into consideration, when looking for a possible cure. Again, all of this demonstrates the importance of research related to zinc and the importance of zinc imaging and the need for fluorescent probes for zinc. With a little optimism, we can even suggest, that screening our ionophores targeting zinc with a novel scaffold as drugs against the infection would not even be a bad idea.

The desired applications for zinc imaging a sensitive, real time measurements are required, with large resolution, which does not destroy tissue in the meantime. Currently the only technique capable of this is optical, fluorescent microscopy. Femtonics LTD is involved in the development and production of or monophoton or multiphoton microscopes for example of two-photon (2P) microscopes, which are the advanced types of fluorescent microscopes.

Despite all the superiorities of these microscopes, the analytes, themselves (in our case, biological zinc) often do not emit fluorescent light, making the imaging impossible without indicator molecules (see documents /7/and/20/ above).

The most important features of sensor molecules are the following:

it can get into cells and stays stable in cells during the measurement it can bind to the analyte in the studied concentration range (zinc, in our case)

it is not fluorescent (or just weakly fluorescent) in free form and it gets fluorescent upon binding to the analyte (the higher the quantum yield, the better. Φ, the quantum yield is a number between 0 and 1 basically representing how strong fluorescence of a compound is. Φ expresses the percentage of absorbed energy, that is emitted in the form of fluorescence)

it is selective towards the analyte (as much as possible)

it is probably not toxic (enabling in vivo experiments)

it absorbs two-photon (further 2P) light in the spectrum emitted by most 2P lasers (~700-1100 nm)

There is a large number of already available fluorescent probes for zinc. However, the criteria required for these sensors in biology create serious problems at designing such molecules. A successful sensor needs to have a fluorescent response for $Zn^{2+}$, while being selective for the most abundant competitive analytes in cells ($Ca^{2+}$, $Mg^{2+}$). The binding of the sensors must be rapid and reversible. The criteria for $K_d$ values vary depending on the region of interest, where the sensor is going to be used and the scope of the measurements. Tunability of $K_d$ in a sensor family is also important, allowing it to be used in a larger number of experiments. Biocompatibility is also important, water-soluble, stable and nontoxic compounds are needed; however, lipophilic probes are also useful for monitoring zinc in vesicles. Insensitivity for pH is also an important design factor according to document /17/. Photophysical properties are also important, such as the wavelength of emission and excitation as well as the quantum yields (Φ), to achieve bright signals. For example for 2P measurements, the wavelength of excitation should be at least above 350 nm, as otherwise, IR lasers will not be able to excite the molecule. In contrast, stokes shift is less important for 2P applications.

The literature presents a variety of biology-based sensors for zinc imaging. I will present these only marginally, as small molecule probes were my main interests.

Peptide sensors are usually Förster resonance energy transfer based sensors (further FRET-based sensors), where zinc finger moieties are coupled with different fluorophores. Another group of peptide-based sensors are made of synthetic oxine (8-hydroxyquinoline, 8-HQ) or dansyl (5-(dimethylamino)naphthalene-1-sulfonyl) containing amino acids. Oxine 7 is a good ionophore for zinc. Dansyl groups coupled to amino acids also work excellent for zinc binding.

Protein-based sensors operate on very similar basics as their peptide-based counterparts; however, they have an advantage in selectivity. In general, these proteins can be natural zinc binding proteins attached to synthetic fluorophores, but there are examples of proteins attached to both synthetic ionophores and fluorophores.

Finally, just to mention, a group of nucleic acid-based sensors also shown in document /17/.

In general, biological probes have their own advantages, that they usually have good properties in biological environments and some of them can be expressed in the cells, moreover, the natural zinc binding motifs have $K_d$ values between 1 pM and 50 μM, which is helpful in measurements, where the concentration change is happening between two very low values. However, their production is often complicated, their tunability is challenging and problems may arise originating from the large bioconjugate structures. The structures can be perturbated at the site of interest, large and complex conformational effects and interactions with the matrix need to be taken into account.

FIG. 9

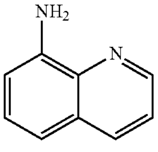

8-aminokinolin
(8-AQ)

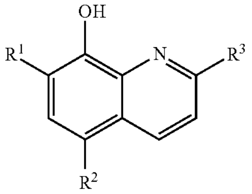

8-hydroxyquinoline
(HQ)

| | |
|---|---|
| R1 = H, R2 = H | R1 = $SO_3H$, R2 = $SO_3H$ |
| R1 = $NO_2$, R2 = H | R1 = $SO_3H$, R2 = $NO_2$ |
| R1 = $NO_2$, R2 = $NO_2$ | R1 = $SO_3NMe_3$, R2 = H |
| R1 = $SO_3H$, R2 = H | R1 = $SO_3NBu_2$, R2 = $SO_3NBu_2$ |
| R3 = H or Me | |

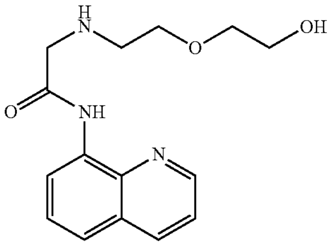

AQZ

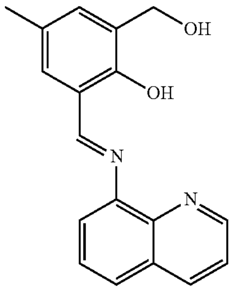

HQMP

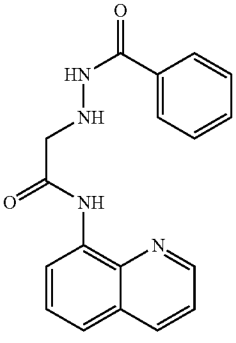

QLNYP

-continued

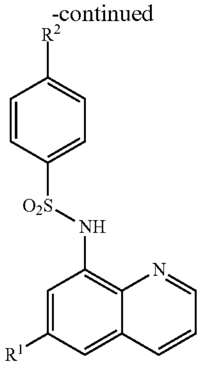

TSQ: R1 = MeO, R2 = $CH_3$
Zinquin acid: R1 = $CH_2COOH$, R2 = $CH_3$
Zinquin ester: R1 = $CH_2COOEt$, R2 = $CH_3$

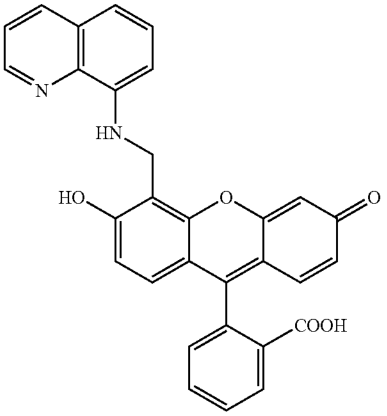

QZ1

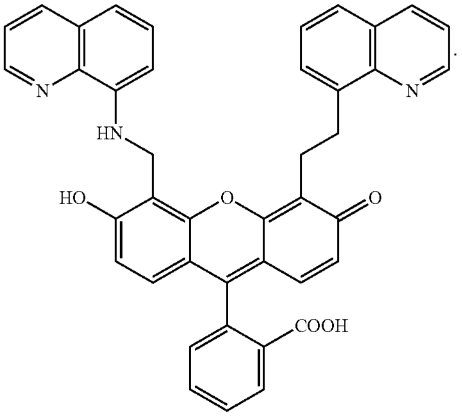

QZ2

Unfortunately, the quinoline type compounds have some drawbacks which are summarized for the exemplified compounds of FIG. 9 as examples in the table below:

| Name | Disadvantages |
|---|---|
| 8-aminoquinoline (further 8-AQ) | Only UV-excitation, low quantum yield, problems arising with complexation in biological media, complexes with higher than 1:1 M:L ratio |
| 8-hydroxyquinoline (further 8-HQ) | Only UV-excitation, low quantum yield, low specificity, no probe combines high quantum yield, high excitation wavelength and good selectivity. |
| AQZ | Only UV-excitation, complexes with higher than 1:1 M:L ratio |

-continued

| Name | Disadvantages |
|---|---|
| HQMP | Poor water-solubility |
| QLNPY | pH sensitive, complexes with higher than 1:1 M:L ratio, not selective for $Cd^{2+}$, quenched by PPi and $S^{2-}$ |
| TSQ | non-1:1 complex, only UV-excitation, poor water-solubility, stored at low temperature |
| Zinquin Acid | Small range of activity (1-2 μM), non-1:1 complex |
| Zinquin Ester | non-1:1 complex, weak solubility, only UV-excitation, poor water-solubility |
| QZ1 | pH sensitive |
| QZ2 | pH sensitive |

The literature contains about 100 compounds are based on quinoline scaffold, which are potentially fluorescent compounds, according to a search on SCIFINDER (2020 December). In these compounds, the 8-amino group quenches the fluorescence by the photoinduced proton/charge transfer to the aromatic nitrogen atom (Internal charge transfer/further ICT/) and photoinduced electron transfer (further PET) phenomena. When the two N atoms bind a metal ion, both effects are blocked, and the fluorescence of the probe is turned on. Many derivatives of 8-AQ were prepared and described in the literature, most of which contain additional ionophore sidechains to improve selectivity, Kd, solubility in water and other properties. The selectivity and $K_d$ values of sensors based on 8-AQ are usually acceptable, however, $Cd^{2+}$, $Cu^{2+}$ and $Fe^{3+}$ ions can compromise these kinds of sensors. 6-methoxy-(8-p-toluenesulfonamido)quinoline (further TSQ) derivatives (as 6 methoxy-(8-p-toluenesulfonamido)quinoline) along its optimized analogues, called Zinquin have a significant drawback. Despite the fact, that they are able to get into cells, their partition is instable, making longer in vivo experiments problematic.

Another larger group of quinoline-based sensors are derivatives of 8-hydroxyquinoline (8 HQ). These compounds share the limitations of previously mentioned probes, moreover, they are less selective for zinc, being rather considered universal chelators according to document /51/ (Prachayasittikul, V. at. al.; Drug Des. Devel. Ther. 2013, 7, 1157-1178). Their spectral properties were optimized by Pearce et al. Imperiali, B. 2001, 5160-5161 /52/. Although compounds with satisfactory excitation wavelengths, selectivity and quantum yield were made, none of them could successfully meet all three criteria. More representatives of these compounds are denoted in the literature, but no great success have been earned on this field.

Dipicolylamine (DPA) is an efficient chelator derived from the highly active chelator TPEN (N,N,N',N'-tetrakis (2-pyridinylmethyl)-1,2-ethanediamine). DPA was consider derivatives the second most important sensors for zinc after quinolines (FIG. 10):

FIG. 10

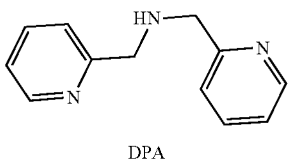

DPA

-continued

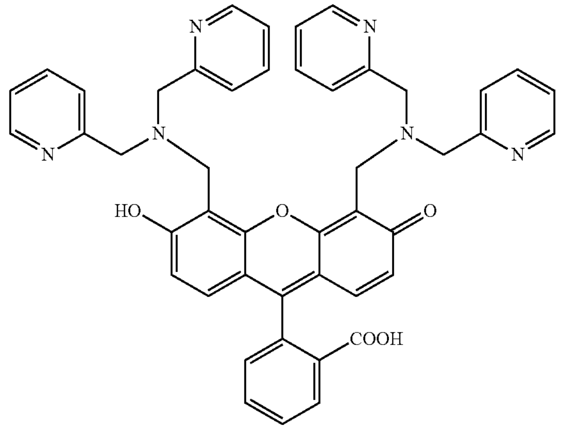

ZinPyr-2

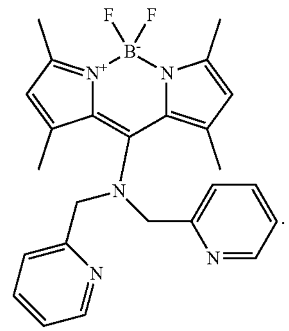

DPA-BODIPY
DPA derivatives

It is straightforward, that DPA is easily linkable to different fluorophores, while having three nitrogen atoms, that can bind to metals. Given the aliphatic nitrogen, which is usable as a linking point, it can act as a quencher based on PET and ICT mechanisms disclosed in document /53/(Xu, Z.; Yoon, J.; Spring, D. R. Chem. Soc. Rev. 2010, 39 (6), 1996-2006). DPA was shown to be selective and efficient chelator for $Zn^{2+}$, moreover, its affinity is tunable based on the electron donating or withdrawing property of the linked fluorophore. DPA was linked with several fluorophores and promising results were achieved with it. The same research group at MIT, which created QZ1 and QZ2 also linked two DPA molecules to fluorescein creating ZinPyr-2, the most basic representative of the ZinPyr (ZP) family of fluorescent probes. This family of sensors consists of 20 derivatives containing one or two ionophores, and different combinations of substituents on the fluorophore and ionophore. The ionophore is also moderated in some cases by changing one of the methylpyridyl groups to aliphatic or other methyl-aromatic substituents. But this compounds also have some disadvantages as follows in table below:

| Name | Disadvantages |
|---|---|
| DPA | non-fluorescent |
| ZinPyr-2 | pH sensitivity |
| DPA-BODIPY | Significant background fluorescence, small fluorescent enhancement |

2,2'-bipyridine (BIPY) and its analogues were reported as zinc sensors in the literature, however, its use is far less popular with a reason. BIPY is rather a universal ionophore, it is less selective and also has worse dissociation constants. Unhindered BIPY analogues in many cases form complexes with higher ligand to metal ratio spoiling the quantitative nature of measurements according to document /53/ above.

Cyclic and acyclic polyamines are widely used metal chelators and large numbers of fluorescent probes are reported incorporating them. However, the selectivity of such ionophores depend on numerous factors, moreover, they are also pH sensitive. Despite some successful representatives, their use is rather limited.

Iminodiacetic acid and its analogues ethylene glycol-bis (2-amino ethylether)-N,N,N',N'-tetraacetic acid (EGTA) and bis(o-aminophenoxy) ethane-N,N,N',N'-tetraacetic acid (BAPTA) have been the most widely used fluorescent probes in calcium imaging according to document of Tsien, R. Y. Biochemistry 1980, 19 (11), 2396-2404 /57/. These compounds were optimized for large selectivity towards $Ca^{2+}$ against $Mg^{2+}$. A good observation is, that in fact, these compounds have larger affinity towards $Zn^{2+}$, than $Ca^{2+}$, however, due to the large excess of calcium compared to $Zn^{2+}$ in biological samples, this is negligible during calcium imaging. Attempts were made to use iminodiacetate analogues and to optimize BAPTA analogues for $Zn^{2+}$ imaging. By removing one or more chelator parts of BAPTA, selectivity towards zinc could be shifted. Similar results were achieved with iminodiacetate analogues. These compounds have shown nanomolar binding constants with zinc ions and their selectivity is not that bad either. However, the achieved selectivity against $Ca^{2+}$ is not enough due to its large concentration rendering these probes unusable for microscopy.

As the prior art shows above, although there are lot of different compounds are reported by different authors, the known compounds have some disadvantageous properties. Although compounds with satisfactory excitation wavelengths, selectivity and quantum yield were made, almost none of them could successfully meet all three criteria. Furthermore, most of compounds are not commercially available or having very high price. Even more, it also important that these compounds should have appropriate solubility in different pH and have to be capable to get into cells. There are a long felt need for compounds which are cheaper and easy to produce and meets the criteria above.

Most of the molecules discussed are currently commercially unavailable for chemical suppliers. Zinquin ester is only currently available at Sigma-Aldrich for a price of 153000 HUF/5 mg, which supports the idea to prepare novel fluorescent dyes with low production costs.

SUMMARY OF THE INVENTION

We found surprisingly that in the case of selection of the new chromophore compounds of the present invention with selected ionophores, new sensor compounds are prepared with very good properties for the one or multiphoton fluorescens microscopy measurement for detecting metals, preferably $Zn^{2+}$ and $Ca^{2+}$ ions in a solution or even living cells, cell culture. According to the present invention the general formula

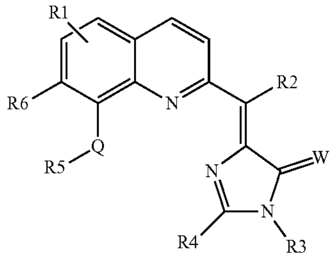

I, wherein

Q stands for —O—$R^5$, —$NR^5R^9$, —S—$R^5$ or —$PR^5R^9$ group

W stands for an O, S atom or =NH or =N—$R^{10}$ group, $R^1$ stands for a H, F, Cl, Br, I, atom, hydroxy, amino, —O-alkyl, —O-aryl, —O-heteroaryl, —O— aralkyl, —O-heteroaralkyl, —S-alkyl, —NH-alkyl, —N-dialkyl, —NH-aryl, —N-diaryl, —NH-heteroaryl, —N-heterodiaryl, —NH-heteroaralkyl, —N-heterodiaralkyl, alkyl, aryl, aralkyl or hetero aralkyl group, $R^2$ stands for a H atom, alkyl, aryl, aralkyl, heteroaralkyl, —$COOR^7$, —$NR^{11}R^8$ group, or $R^2$ and $R^1$ together form an izocyclic or heterocyclic ring, $R^3$ stands for a H atom, alkyl, aryl group, $R^4$ stands for a H atom, —O-alkyl, —NH-alkyl, —NH-aryl, alkyl, aryl, aralkyl, heteroaralkyl, heterocyclic alkyl, heteroaryl group, $R^5$, $R^6$, $R^7$, $R^8$, $R^9$, $R^{10}$ or $R^{11}$ independently stand for a H atom, alkyl, aryl group, heteroaralkyl group, aralkyl group or $R^5$ and $R^6$ form a heterocyclic ring preferably pyridine, pyrrol, piperidine or phenanthroline, $R^5$ and $R^9$ form a double bond connected to an alkyl group or form a heterocyclic ring preferably azetidine, pyrrolidine, piperidine, piperazine, morpholine with $R^6$.

and salts and complexes thereof.

These compounds can be prepared by reaction of a substituted 3,5-dihydro-4H-imidazol-4-one substituted with an with a substituted aromatic aldehyde compound. The thus obtained compound can be used for sensor for imaging of the zinc concentration of solutions, living cells or cell cultures with mono or multiphoton microscopy tests with high efficacy.

DETAILED DESCRIPTION OF THE INVENTION

A chemical synthesis for the chromophore, p-HOBDI, ((5-(4-hydroxybenzylidene)-2,3-dimethyl-3,5-dihydro-4H-imidazol-4-one, (17) and investigation of tunability of its fluorescence is disclosed Jancsó, A.; Kovács, E.; Cseri, L.; Rózsa, B. J.; Galbács, G.; Csizmadia, I. G.; Mucsi, Z. Spectrochim. Acta Part A Mol. Biomol. Spectrosc. 2019, 218, 161-170. /10/).

Scheme 1.

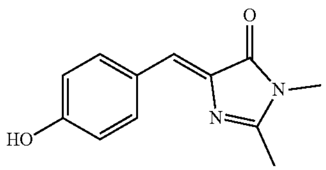

17: p-HOBDI
The scaffold of ZP sensors

-continued

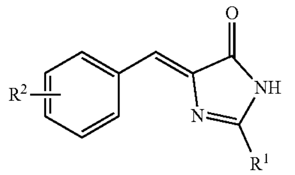

17a: $R^1$ = NHPh, $R^2$ = 4-AcNH $\Phi_{rel}$ = 27.5
17b: $R^1$ = NHPh, $R^2$ = 4-Cl $\Phi_{rel}$ = 23.0
17c: $R^1$ = NHPh, $R^2$ = COOH $\Phi_{rel}$ = 23.1
17 more analogues $\Phi_{rel}$ = 2.5 to 22

In this paper a new and effective synthesis route for GFP analogues was also reported (Scheme 2) from 2-thiohydantoin (18), which is treated with NaH in dry N,N-Dimethylformamide (further DMF) (18b), and the deprotonated form is carried into a one-pot methylation by MeI to yield S-methylthiohydantoin (19).

Scheme 2.

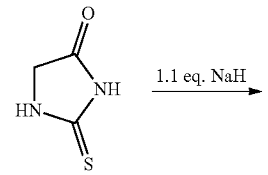

2-thiohydantoin
18

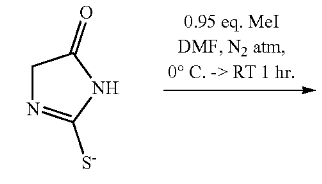

2-thiohydantoinate
18b

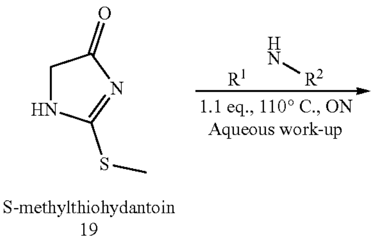

S-methylthiohydantoin
19

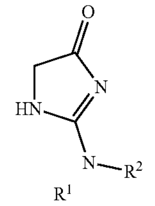

2-amino-imidazol-4-one
derivatives
20

-continued

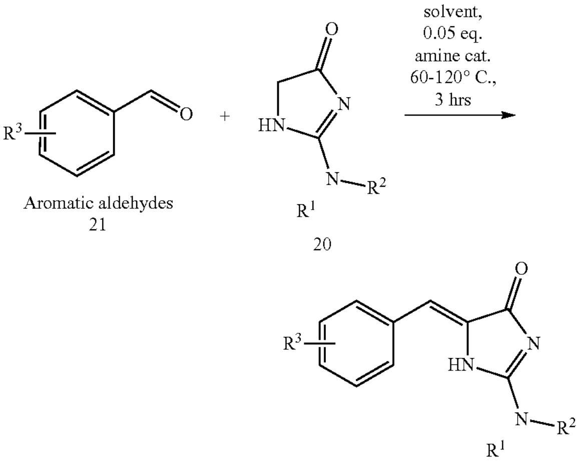

Aromatic aldehydes
21

20

17 d
GFP-chromophore derivatives

This is followed by the one-pot addition of the desired amine compound resulting in the desired 2-amino substituted of imidazol-4-ones (20) after an aqueous work-up and purification. The resulting product 20 is then reacted with aromatic aldehydes in a Knoevenagel condensation to yield analogues of 17. The modification of this synthetic route by changing benzaldehydes to 2-quinolinecarbaldehyde derivatives, a unsubstituted or substituted aminoquinoline or hydroxyquinoline derivatives very effective sensors molecules are produced. These sensors are proved to be suitable for using in fluorescence microscopy either in one or multiphoton tests, preferably in two photon (2P) microscopy. Thus, we found surprisingly that compounds of general formula

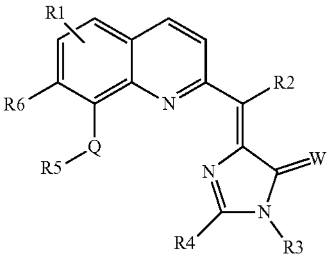

I, wherein

Q stands for an —O—$R^1$, —$NR^5R^9$, —S—$R^5$ or —$PR^5R^9$ group

W stands for an O, S atom or =NH or =N—$R^{10}$ group, $R^1$ stands for a H, F, Cl, Br, I atom, hydroxy, amino, —O-alkyl, —O-aryl, —O-heteroaryl, —O— aralkyl, —O-heteroaralkyl, —S-alkyl, —NH-alkyl, —N-dialkyl, —NH-aryl, —N-diaryl, —NH-heteroaryl, —N-heterodiaryl, —NH-heteroaralkyl, —N-heterodiaralkyl, alkyl, aryl, aralkyl or hetero aralkyl group, $R^2$ stands for a H atom, alkyl, aryl, aralkyl, heteroaralkyl, —$COOR^7$, —$NR^{11}R^8$ group, or $R^2$ and $R^1$ together form an izocyclic or heterocyclic ring, $R^3$ stands for a H atom, alkyl, aryl group, $R^1$ stands for a H atom, —O-alkyl, —NH-alkyl, —NH-aryl, alkyl, aryl, aralkyl, heteroaralkyl group, $R^5$, $R^6$, $R^7$, $R^8$, $R^9$, $R^{10}$ or $R^{11}$ independently stand for a H atom, alkyl, preferably Me, Et, cyclohexyl, —$CH_2$—

$CH_2$—$NMe_2$, —$CH_2$—$CH_2$—$N(CH_2Pyr)_2$, group, aryl group, preferably phenyl, heteroaralkyl group, preferably methylpyridyl aralkyl, heterocyclic alkyl ($C_3$-$C_5$), azetidine, pyrrolidine, piperidine, piperazine, morpholine heteroaryl group, preferably pyridyl, group or $R^5$ and $R^6$ form a heterocyclic ring, preferably pyridine, phenanthroline, pyrrole, piperidine or $R^5$ and $R^9$ form a double bond connected to an alkyl group or form a heterocyclic, preferably azetidine, pyrrolidine, piperidine, piperazine, morpholine ring with $R^6$, and salts and complexes thereof.

According to present invention, the meaning of the e.g. hydroxy, amino, —O-alkyl, —O-aryl, —O-heteroaryl, —O-aralkyl, —O-heteroaralkyl, —S-alkyl, —NH-alkyl, —N-dialkyl, —NH-aryl, —N-diaryl, —NH-heteroaryl, —N-heterodiaryl, —NH-heteroaralkyl, —N-heterodiaralkyl, alkyl, aryl, aralkyl or hetero aralkyl group are well known for the person killed in the art from the general knowledge of the organic chemistry. For the clarity we are summarized the meanings of mentioned substituents above as follows.

According to the present invention alkyl groups means saturated and unsaturated alkyl groups which can contain doble or triple C—C bounds, furthermore alkyl groups can be straight, branched or cyclic, the lengths of alkyl groups preferably, $C_1$-$C_8$, more preferably $C_1$-$C_6$, most preferably $C_1$-$C_4$. Most preferably unsubstituted or substituted methyl, ethyl, propyl, izopropyl n-butyl, sec-butyl, tert-butyl, as cyclic alkyl group e.g. cyclopropyl, cyclohexyl can be used. These alkyl groups can be substituted with other alkyl groups, aryl groups, having one or more fused ring and the rings can contain one or more N, O or S atoms, aralkyl groups, one or more halogens, such as Cl, Br, I and Fluor atoms, substituted hydroxy groups, cyano groups, acyl groups, amino-carbonyl groups, carboxyl groups and alkoxy-carbonyl groups, primer or seconder amino groups, saturated or unsaturated isocyclic and heterocyclic groups, which heterocyclic groups can contain one or more N, O or S atoms. The alkyl groups are preferably substituted with primer or seconder amin groups e.g. with amino group, amino groups substituted with one or two $C_1$-$C_4$ alkyl groups, aralkyl groups, such a benzyl group, or hetero aralkyl groups such as methyl-pyridyl group, or carboxyl groups, alkyl or aryl ester groups, substituted hydroxy groups or hydroxy groups.

Most preferable alkyl groups are methyl, ethyl, propyl, i-propyl, butyl, t-butyl-methylpyridyl-, —CH2COOH, —CH2-CH2-NMe2 group.

According to the present invention —O-alkyl groups are connected to the structure with an oxygen atom which oxygen atom is substituted with an above defined alkyl group.

Most preferable —O-alkyl groups are OH, —O-methyl, —O—$CH_2$—$CH_2$—$NMe_2$, O-methylpyridyl group.

According to the present invention —S-alkyl groups are connected to the structure with a sulfur atom which sulfur atom is substituted with an above defined alkyl group.

Most important —O-alkyl groups are —S—H, —S-Me, —S—$CH_2$—$CH_2$—$NMe_2$, S-methylpyridyl group.

According to the present invention —N-alkyl groups are connected to the structure with a nitrogen atom which nitrogen is substituted with one or two above defined alkyl group.

Most important —N-alkyl groups are —N—H, —N-Me, —$NMe_2$, -azetidine, pyrrolidine, piperidine, morpholine, piperazine and derivatives, N—$CH_2$—$CH_2$—$NMe_2$. N-methylpyridyl, N-bis(methylpyridyl) group.

According to the present invention aryl groups are isocyclic groups which comprises a mono or fused polycyclic aromatic group, such as phenyl, naphthalenyl groups. These aryl groups of present invention can be unsubstituted or substituted. Aryl groups of the present invention can be substituted optionally with alkyl groups as defined above, further aryl groups, groups having one or more fused ring and the rings can contain one or more N, O or S atoms, aralkyl groups, one or more halogens, such as Cl, Br, I and fluor atoms, substituted hydroxy groups, hydroxy groups, cyano groups, acyl groups, amino-carbonyl groups, carboxyl groups and alkoxy-carbonyl groups, primer or seconder amino groups, saturated or unsaturated isocyclic and heterocyclic groups, which heterocyclic groups can contain one or more N, O or S atoms. The aryl groups preferably substituted with primer or seconder amino groups e.g. with amino group, amino groups substituted with one or two $C_1$-$C_4$ alkyl groups, aralkyl groups, such a benzyl group, or hetero aralkyl groups such as methyl-pyridyl group, or carboxyl groups, alkyl or aryl ester groups, substituted hydroxy groups or hydroxy groups.

Most preferable substituents of aryl groups are F, Cl, cyano, $C_1$-$C_4$ alkyl groups, benzyl group, methyl-pyridyl carboxyl groups, alkyl or aryl ester groups, substituted hydroxy groups or hydroxy groups.

According to the present invention —O-aryl groups are connected to the structure with an oxygen atom which oxygen atom is substituted with an above defined aryl group.

Most preferable substituents of —O-aryl groups are —O-phenyl, —O— pyridyl groups.

According to the present invention —S-aryl groups are connected to the structure with a sulfur atom which sulfur atom is substituted with an above defined aryl group.

Most preferable substituents of —S-aryl groups are S-phenyl, S-pyridyl group.

According to the present invention —N-aryl groups are connected to the structure with a nitrogen atom which nitrogen is can be substituted with one above defined aryl and optionally the amino group is even substituted with another group which is different from aryl group.

Most preferable substituents of —N-aryl groups are N-phenyl, N-pyridyl, N-methyl pyridyl group.

According to the present invention —N-diaryl groups are connected to the structure with a nitrogen atom which nitrogen is substituted with two same or different above defined aryl group.

Most preferable substituents of —N-diaryl groups are N,N-diphenyl, N,N-dipyridyl group.

According to the present invention aralkyl groups are isocyclic groups which are mono or fused polycyclic aromatic group, such as phenyl, naphthalenyl groups and which groups are attached to the compound by an alkylene group, such as methylene group. These aralkyl groups of present invention can be unsubstituted or substituted. Substituents can be attached to the alkyl and/or to the aromatic ring. Aralkyl groups of the present invention can be substituted optionally with alkyl groups as defined above, further aryl groups as defined above, groups having one or more fused ring and the rings can contain one or more N, O or S atoms, aralkyl groups, one or more halogens, such as Cl, Br, I and Fluor atoms, substituted hydroxy groups, hydroxy groups, cyano groups, acyl groups, amino-carbonyl groups, carboxyl groups and alkoxy-carbonyl groups, primer or seconder amino groups, saturated or unsaturated isocyclic and heterocyclic groups, which heterocyclic groups can contain one or more N, O or S atoms. The aralkyl groups preferably substituted with primer or seconder amino groups e.g. with amino group, amino groups substituted with one or two $C_1$-$C_4$ alkyl groups, aralkyl groups, such a benzyl group, or hetero aralkyl groups such as methyl-pyridyl group, carboxyl groups, alkyl or aryl ester groups, substituted hydroxy groups or hydroxy groups.

Most important specials are quinoline, pyridine, phenanthroline, benzol, isoquinoline, coumarine, indole, benzimidazol, izoindole, benzothiophene, benzofuranyl group.

According to the present invention —O-aralkyl groups are connected to the structure with an oxygen atom which oxygen atom is substituted with an above defined aralkyl group.

Most preferable substituents of —O-aralkyl groups are O-methylpyridyl, O-benzyl group.

According to the present invention —S-aralkyl groups are connected to the structure with a sulfur atom which sulfur atom is substituted with an above defined aralkyl group.

Most preferable substituents of —S-aralkyl groups are S-methylpyridyl, S-benzyl, S-methylnaphtyl group.

According to the present invention —N-aralkyl groups are connected to the structure with a nitrogen atom which nitrogen is can be substituted with one above defined aralkyl and optionally the—group is even substituted with another group which is different from aralkyl group.

Most preferable substituents of —N-aralkyl groups are N-methyl pyridyl, N-benzyl, N-methylnaphtyl group.

According to the present invention —N-diaryl groups are connected to the structure with a nitrogen atom which nitrogen is substituted with two same or different above defined aralkyl group.

Most preferable substituents of —N-diaryl groups are N,N-dimethyl pyridyl, N,N-dibenzyl group.

According to the present invention heteroaryl groups are heterocyclic groups which comprise mono or fused polycyclic aromatic group containing at least one heteroatom selected from N, O, S. such group for example pyridyl or quinoline groups. These heteroaryl groups of present invention can be unsubstituted or substituted. Aryl groups of the present invention can be substituted optionally with alkyl groups as defined above, aryl groups as defined above, further groups having one or more fused ring and the rings can contain one or more N, O or S atoms, aralkyl groups, one or more halogens, such as Cl, Br, I and fluor atoms, substituted hydroxy groups, hydroxy groups, cyano groups, acyl groups, amino-carbonyl groups, carboxyl groups and alkoxy-carbonyl groups, primer or seconder amino groups, saturated or unsaturated isocyclic and heterocyclic groups, which heterocyclic groups can contain one or more N, O or S atoms. Heteroaryl groups preferably substituted with primer or seconder amino groups e.g. with amino group, amino groups substituted with one or two $C_1$-$C_4$ alkyl groups, aralkyl groups, such a benzyl group, or hetero aralkyl groups such as methyl-pyridyl group, or carboxyl groups, alkyl or aryl ester groups, substituted hydroxy groups, hydroxy groups.

Most preferable substituents of heteroaryl groups are —N-aralkyl groups are quinoline, isoquinoline, indole, benzimidazole group, According to the present invention —O-heteroaryl groups are connected to the structure with an oxygen atom which oxygen atom is substituted with an above defined heteroaryl group.

Most preferable substituents of —O-heteroaryl groups is O-pyridyl group.

According to the present invention —S-heteroaryl groups 1 groups are connected to the structure with a sulfur atom which sulfur atom is substituted with an above defined heteroaryl groups.

Most preferable substituents of —S-heteroaryl groups is —S-pyridyl group.

According to the present invention —N-heteroaryl groups are connected to the structure with a nitrogen atom which nitrogen is can be substituted with one above defined heteroaryl groups and optionally the amino group is even substituted with another group which is different.

Most preferable substituents of is-N-heteroaryl groups is N-pyridyl group.

According to the present invention —N-di heteroaryl groups are connected to the structure with a nitrogen atom which nitrogen is substituted with two same or different above defined heteroaryl groups.

Most preferable substituents of is —N,N-heteroaryl groups is N,N-dipyridyl group.

According to the present invention hetero-aralkyl groups are heterocyclic groups which comprise mono or fused polycyclic aromatic group containing at least one heteroatom selected from N, O, S such group for example pyridyl or quinoline groups which are attached to the compound by an alkylene group, such as methylene group. These hetero-aralkyl groups of present invention can be unsubstituted or substituted. Substituents can be attached to the alkyl and/or to the aromatic ring. Hetero-aralkyl groups of the present invention can be substituted optionally with alkyl groups as defined above, further aryl groups as defined above, groups as defined above having one or more fused ring and the rings can contain one or more N, O or S atoms, further hetero-aralkyl groups, one or more halogens, such as Cl, Br, I and Fluor atoms, substituted hydroxy groups, hydroxy groups, cyano groups, acyl groups, amino-carbonyl groups, carboxyl groups and alkoxy-carbonyl groups, primer or seconder amino groups, saturated or unsaturated isocyclic and heterocyclic groups, which heterocyclic groups can contain one or more N, O or S atoms. The aralkyl groups preferably substituted with primer or seconder amino groups e.g. with amino group, amino groups substituted with one or two $C_1$-$C_4$ alkyl groups, aralkyl groups, such a benzyl group, or hetero aralkyl groups such as methyl-pyridyl group, carboxyl groups, alkyl or aryl ester groups, substituted hydroxy groups or hydroxy groups.

According to the present invention —O-hetero-aralkyl groups are connected to the structure with an oxygen atom which oxygen atom is substituted with an above defined hetero-aralkyl group.

Most preferable substituent of is-O-heteroaryl groups is O-methylpyridyl group.

According to the present invention —S-hetero-aralkyl groups are connected to the structure with a sulfur atom which sulfur atom is substituted with an above defined hetero-aralkyl group.

Most preferable substituent of is-S-heteroaryl groups is S-methylpyridyl group.

According to the present invention —N-hetero-aralkyl groups are connected to the structure with a nitrogen atom which nitrogen is can be substituted with one above defined hetero-aralkyl and optionally the amino group is even substituted with another group which is different from hetero-aralkyl group.

Most preferable substituent of is-N-heteroaryl groups is N-methylpyridyl group.

According to the present invention —N-di-hetero-aralkyl groups are connected to the structure with a nitrogen atom which nitrogen is substituted with two same or different above defined hetero-aralkyl group.

Most preferable substituent of is —N— diheteroaryl groups is N,N-dimethylpyridyl group.

According to the present invention isocyclic rings comprise only carbon atoms, these rings can be saturated partly saturated or aromatic. The isocyclic compounds can be mono or fused polycyclic compound. Aliphatic isocyclic rings e.g. cyclopropane, cyclohexane, or cyclooctane, aromatic compounds such as benzol, toluene, naphthalene. According to the present invention these rings are substituted. These isocyclic rings are parts of the structures of the compounds of the present invention. Isocyclic parts of the compounds of the present invention can be substituted groups of alkyl groups as defined above, aryl groups as defined above, groups as defined above having one or more fused ring and the rings can contain one or more N, O or S atoms, hetero-aralkyl groups, one or more halogens, such as Cl, Br, I and fluor atoms, substituted hydroxy groups, hydroxy groups, cyano groups, acyl groups, amino-carbonyl groups, carboxyl groups and alkoxy-carbonyl groups, primer or seconder amino groups, saturated or unsaturated isocyclic and heterocyclic groups, which heterocyclic groups can contain one or more N, O or S atoms. The isocyclic parts of the compounds of the present invention preferably substituted with primer or seconder amino groups e.g. with amino group, amino groups substituted with one or two $C_1$-$C_4$ alkyl groups, aralkyl groups, such a benzyl group, or hetero aralkyl groups such as methyl-pyridyl group, carboxyl groups, alkyl or aryl ester groups, substituted hydroxy groups or hydroxy groups.

According to the present invention heterocyclic rings comprise at least one heteroatom selected from N, S, O. These rings can be saturated partly saturated or aromatic. The heterocyclic rings can be mono or fused polycyclic, heterocyclic rings can be saturated as piperazine, or piperidine but can be aromatic such as pyridine. According to the present invention these rings can be substituted. These heterocyclic rings are parts of the structures of the compounds of the present invention. Heterocyclic part of the compounds of the present invention can be substituted groups of alkyl groups as defined above, aryl groups as defined above, 1 groups as defined above having one or more fused ring and the 1 rings can contain one or more N, O or S atoms, hetero-aralkyl groups, one or more halogens, such as Cl, Br, I and Fluor atoms, substituted hydroxy groups, hydroxy groups, cyano groups, acyl groups, amino-carbonyl groups, carboxyl groups and alkoxy-carbonyl groups, primer or seconder amino groups, saturated or unsaturated isocyclic and heterocyclic groups, which heterocyclic groups can contain one or more N, O or S atoms. The isocyclic parts of the compounds of the present invention preferably substituted with primer or seconder amino groups e.g. with amino group, amino groups substituted with one or two $C_1$-$C_4$alkyl groups, aralkyl groups, such a benzyl group, or hetero aralkyl groups such as methyl-pyridyl group, carboxyl groups, alkyl or aryl ester groups, substituted hydroxy groups or hydroxy groups.

More preferably the present invention relates compounds of formula I wherein

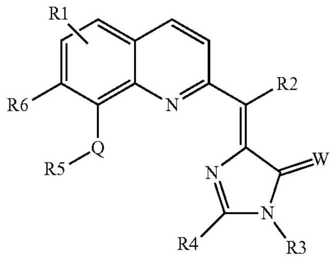

Q stands for —O—$R^5$; —S—R5; or —$NR^5R^9$ or —$PR^5R^9$ group

W stands for an O, S atom, $R^1$ stands for a H, F, Cl, Br, I atom, hydroxy, amino, —O-alkyl, —O-aryl, —O-heteroaryl, —O— aralkyl, —O-heteroaralkyl, —S-alkyl, —NH-alkyl, —N-dialkyl, —NH-aryl, —N-diaryl, —NH-heteroaryl, —N-heterodiaryl, —NH-heteroaralkyl, —N-heterodiaralkyl, alkyl, aryl, aralkyl or hetero aralkyl group, $R^2$ stands for a H atom, alkyl, aryl, aralkyl, heteroaralkyl, —$COOR^7$, —$NR^{11}R^8$ group, or $R^2$ and $R^1$ together form an izocyclic or heterocyclic ring, $R^3$ stands for a H atom, alkyl, aryl group, $R^4$ stands for a H atom, —O-alkyl, —NH-alkyl, —NH-aryl, alkyl, aryl, aralkyl, heteroaralkyl, heterocyclic alkyl, heteroaryl group, $R^5$, $R^6$, $R^7$, $R^8$, $R^9$, $R^{10}$ or $R^{11}$ independently stand for a H atom, alkyl, preferably Me, Et, cyclohexyl, —$CH_2$—$CH_2$—$NMe_2$. —$CH_2$—$CH_2$—$N(CH_2Pyr)_2$, aryl group, preferably phenyl, heteroaralkyl group, preferably methylpyridyl aralkyl, heterocyclic alkyl ($C_3$-$C_5$), azetidine, pyrrolidine, piperidine, piperazine, morpholine heteroaryl group, preferably pyridyl, group or $R^5$ and $R^6$ form a heterocyclic ring, preferably pyridine, phenanthroline, pyrrole, piperidine or $R^5$ and $R^9$ form a double bond connected to an alkyl group or form a heterocyclic, preferably azetidine, pyrrolidine, piperidine, piperazine, morpholine ring with $R^6$, and salts and complexes thereof.

More preferably, the present invention relates of compounds of general formula I wherein Q stands for —O—$R^5$ or —$NR^5R^9$ group W stands for an O or S atom, $R^1$, $R^2$, $R^3$, $R^6$, $R^7$, $R^8$, $R^{10}$ and $R^{11}$ stands for a H, F, Cl, Br, I, $R^1$ stands for a —O-alkyl, —NH-alkyl, —NH-aryl group, $R^5$, $R^9$, independently stand for a H atom, alkyl, aryl group, or $R^5$ and $R^6$ form a heterocyclic ring, preferably pyridine, phenanthroline, pyrrole, piperidine or $R^5$ and $R^9$ form a double bond connected to an alkyl group, or form a heterocyclic ring preferably pyridine, phenanthroline, pyrrole, piperidine ring with group $R^6$.

Most preferably the present invention relates of compounds of the general formula I wherein Q stands for —O—$R^5$ or —$NR^5R^9$ group, W stands for an O atom, $R^1$, $R^2$, $R^3$, $R^6$, $R^7$, $R^8$, $R^{10}$ and $R^{11}$ stands for a H atom, $R^1$ stands for an —NH-aryl group, preferably phenylamino group, $R^5$, $R^9$, independently stand for a H atom, alkyl, preferably methyl group carboxymethyl group, or $R^5$ and $R^6$ form a heterocyclic, preferably azetidine, pyrrolidine, piperidine, piperazine, morpholine or $R^5$ and $R^9$ form a double bond connected to an alkyl group, or form a heterocyclic ring, preferably azetidine, pyrrolidine, piperidine, piperazine, morpholine ring with $R^6$, preferably a substituted or unsubstituted fused pyridine ring.

According to the present invention we have same very useful and advantageous special embodiments of the compound of formula I of the present invention as follows:

28

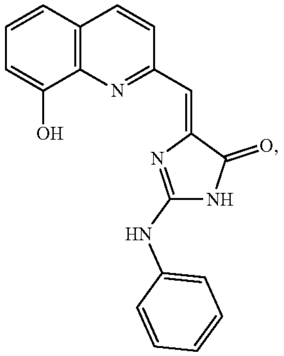

32

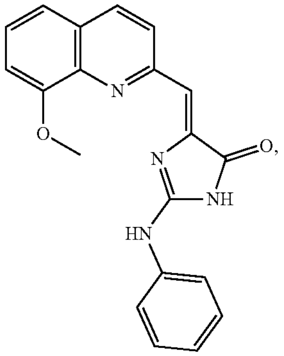

29

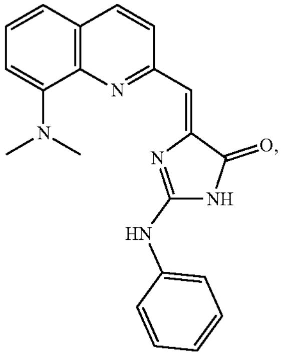

-continued

31

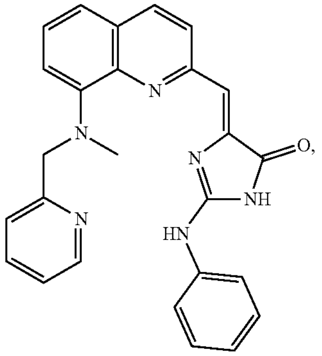

30

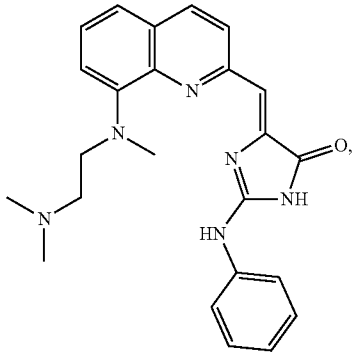

33

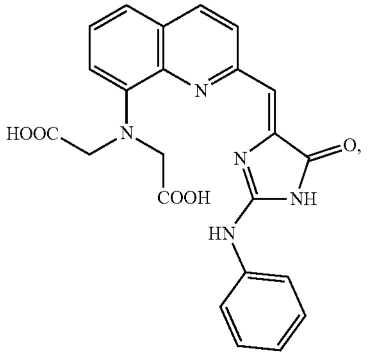

34

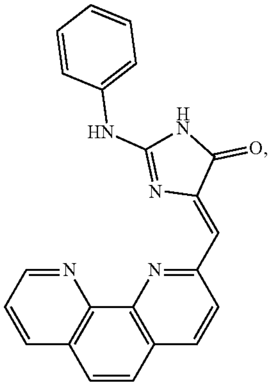

-continued

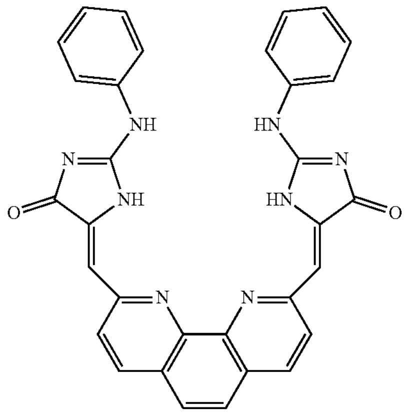

and salts and complexes thereof.

The meanings of the substituents of preferable embodiments of the present invention are well known from the basic knowledge of the person skilled in the art. More preferable examples of organic groups of substituents are defined above.

According to another preferred embodiment of the present invention are salts of the compounds of the general formula I. These salts may be stochiometric or non-stochiometric.

The ratio of the compound of general formula I and the salt forming compounds basically depends on the number of ionizable groups of compounds of general formula I and the number of ionizable groups of the salt forming compound. For example, if the compound of formula I comprises two amino groups, it is expected that it can form a monovalent salt forming compound, a 1:1 and 1:2 salts can be achieved depending on the added amount of monovalent salt forming compound. Otherwise, steric effects, or the strengths of the ionizable groups of the compounds of formula I and/or the salt forming compounds also can influence the stochiometric form of the obtained salt. The person skilled in the art can predict the stochiometric form of the obtained salt based on the structure of the compound of formula I, the used salt forming agent properties and the process for preparation thereof. As salt forming compounds can be used organic or inorganic acids or bases.

As salt forming agent organic acidic compounds can be used e.g. aliphatic or aromatic acids, heteroaromatic acids, saturated or unsaturated aliphatic, alicyclic, or heterocyclic acids. The used acids can be mono valent, which means that the compound comprises one carboxyl group or sulfonic acid group only, polyvalent, which means that the used organic acid comprises more than one carboxylic or sulfonic acid group, or a one or more from them. Example for monovalent aliphatic acids acetic acid, propionic acid, trifluoro acetic acid, dichloroacetic acid, acrylic acid, metacrylic acid, monovalent sulfonic acids e.g. methanesulfonic acid, ethanesulfonic acid, bivalent or polyvalent aliphatic acids e.g. oxalic acid, malonic acid butanedioic acid, fumaric acid citric acid, heterocyclic acid, mono, bi or polyvalent aromatic carboxylic acids e.g. benzoic acid salicylic acid, benzenesulfonic acid, para-toluenesulfonic acid, phtalic acid. Most preferably acetic acid, oxalic acid, fumaric acid, maleic acid, trifluoracetic acid, methansulfonic acid, para-toluenesulfonic acid, benzoic acid, phthalic acid, terephthalic acid, are used.

As salt forming agent inorganic acids such as HCl, HBr, HF, HI, Sulfur containing such as sulphuric acid phosphor containing acids, such as phosphoric acid, and nitrogen containing acids such as nitric acid also can be used. Most preferably, HCl, HBr, HI, HF, $H_2SO_4$, $HNO_3$, $H_3PO_4$ are used.

In the case of the present general formula I comprises acidic, preferably carboxyl groups, salts can be prepared by using organic and inorganic bases. As organic base amines, primary, secondary or tert. amins, as inorganic base, metal hydroxides, carbonates, hydroxycarbonates preferably alkali, alkali earth metal or transitional earth metal hydroxides, carbonates, hydroxycarbonates can be used. Most preferably sodium or potassium carbonate are used.

Another embodiment of the present invention is a complex of compounds of the general formula I wherein the complex forming compound is a $Zn^{2+}$ ion. These complexes are stochiometric, and depending of the structure of Compound of general formula I the ratio of the compound of the general formula I and $Zn^{2+}$ ion is 1:1 or 1:2, most preferably 1:1.

Another aspect of the present invention is a process for the preparation of the compound of the general formula I or a salt or a complex thereof, characterized in that a compound of general formula

II

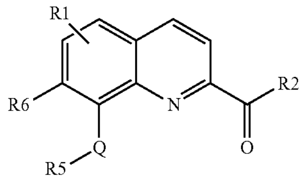

wherein:

Q stands for —O—$R^5$, —$NR^5R^9$, —S—$R^5$ or —$PR^5R^9$ group, preferably Q stands for —O—$R^8$ or —$NR^5R^9$ group, $R^1$ stands for a H atom, F, Cl, Br, I, hydroxy, amino, —O-alkyl, —O-aryl, —O-heteroaryl, —O— aralkyl, —O-hetero-aralkyl, —S-alkyl, —NH-alkyl, —N-dialkyl, —NH-aryl, —N-diaryl, —NH-heteroaryl, —N-heterodiaryl, —NH-hetero-aralkyl, —N-heterodiaralkyl, alkyl, aryl, aralkyl or hetero aralkyl group, preferably $R^1$ stands for a H atom, hydroxy, amino, —O-alkyl, —O-aryl, —S-alkyl, —NH-alkyl, —N-dialkyl, alkyl, aryl, aralkyl group, more preferably $R^1$ stands for a H atom, $R^2$ stands for a H atom, alkyl, aryl, aralkyl, hetero-aralkyl, —$COOR^7$, —$NR^{11}R^8$ group, preferably $R^2$ stands for a H, alkyl, aryl, —$COOR^7$, —$NR^{11}R^8$ group, more preferably $R^2$, stands for a H atom, or $R^2$ and $R^1$ together form an isocyclic or heterocyclic ring, $R^5$, $R^6$, $R^7$, $R^8$, $R^9$, $R^{10}$ or $R^{11}$ independently stand for a H atom, alkyl group, preferably Me, Et, cyclohexyl, —$CH_2$—$CH_2$—$NMe_2$. —$CH_2$—$CH_2$—$N(CH_2Pyr)_2$, aryl group, preferably phenyl group, hetero-aralkyl group, preferably methylpyridyl, heterocyclic alkyl ($C_3$-$C_5$), azetidine, pyrrolidinyl, piperidinyl, piperazinyl, morpholinyl groups, aralkyl group or, preferably $R^5$, $R^6$, $R^7$, $R^8$, $R^9$, $R^{10}$ or $R^{11}$ independently stand for a H atom, alkyl, aryl group, more preferably $R^1$, $R^2$, $R^3$, $R^6$, $R^7$, $R^8$, $R^{10}$ and $R^{11}$ stands for a H atom, or $R^5$ and $R^6$ form a heterocyclic ring, or $R^5$ and $R^9$ form a double bond connected to an alkyl group or form a heterocyclic ring preferably pyridine, phenanthroline, pyrrole, piperidine ring with $R^6$, is reacted with the compound of general formula

III

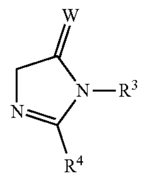

W stands for an O or S atom, =NH or =N—$R^{10}$ group, preferably W stands for an O or S atom, more preferably W stands for an O atom, $R^3$ stands for a H atom, alkyl, aryl group, preferably $R^3$ stands for a H atom, $R^4$ stands for a H atom, —O-alkyl, —NH-alkyl, —NH-aryl, alkyl, aryl, aralkyl, hetero-aralkyl heterocyclic alkyl, heteroaryl group, preferably $R^1$ stands for, —O-alkyl, —NH-alkyl, —NH-aryl group, more preferably $R^4$ stands for an —NH-aryl group, most preferably phenylamino group, then the thus obtained compound of general formula wherein

I

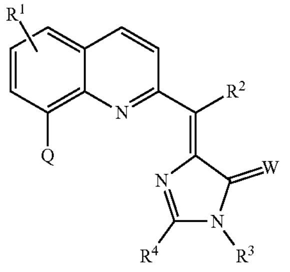

wherein

Q stands for —O—$R^5$, —$NR^5R^9$, —S—$R^5$ or —$PR^5R^9$ group, preferably Q stands for —O—$R^8$ or —$NR^8R^9$ group, W stands for an O or S atom, =NH or =N—$R^{10}$ group, preferably W stands for an O or S atom, more preferably W stands for an O atom, $R^1$ stands for a H, F, Cl, Br or I atom, hydroxy, amino, —O-alkyl, —O-aryl, —O-heteroaryl, —O— aralkyl, —O-hetero-aralkyl, —S-alkyl, —NH-alkyl, —N-dialkyl, —NH-aryl, —N-diaryl, —NH-heteroaryl, —N-heterodiaryl, —NH-hetero-aralkyl, —N-heterodiaralkyl, alkyl, aryl, aralkyl or hetero aralkyl group, preferably $R^1$ stands for a H atom, hydroxy, amino, —O-alkyl, —O-aryl, —S-alkyl, —NH-alkyl, —N-dialkyl, alkyl, aryl, aralkyl group, more preferably $R^1$ stands for a H atom, $R^2$ stands for a H atom, alkyl, aryl, aralkyl, hetero-aralkyl, —$COOR^7$, —$NR^{11}R^8$ group, preferably $R^2$ stands for a H atom, alkyl, aryl, —$COOR^7$, —$NR^{11}R^8$ group, more preferably $R^2$, stands for a H atom, or $R^2$ and $R^1$ together form an isocyclic or heterocyclic ring, $R^3$ stands for a H atom, alkyl, aryl group, $R^4$ stands for a H atom, —O-alkyl, —NH-alkyl, —NH-aryl, alkyl, preferably Me, Et, cyclohexyl, —$CH_2$—$CH_2$—$NMe_2$. —$CH_2$—$CH_2$—$N(CH_2Pyr)_2$, group, aryl, aralkyl, hetero-aralkyl group, $R^5$, $R^6$, $R^7$, $R^8$, $R^9$, $R^{10}$ or $R^{11}$ independently stand for a H atom, alkyl, aryl group, preferably phenyl group, hetero-aralkyl group, preferably methylpyridyl group, aralkyl group, heterocyclic alkyl ($C_3$-$C_5$), azetidinyl, pyrrolidinyl, piperidinyl, piperazinyl, morpholinyl groups, heteroaryl group, preferably pyridyl, group or $R^5$ and $R^6$ form a heterocyclic ring, preferably pyridine, phenanthroline, pyrrole, piperidine ring or $R^5$ and $R^9$ form a double bond connected to an alkyl group or form a heterocyclic ring, preferably azetidine, pyrrolidine, piperidine, piperazine, morpholine ring with group $R^6$, isolated or optionally with or without isolation transformed into salt or complex form.

The process is a condensation of a compound of a heterocyclic aldehyde of general formula II and the dihydroimidazole derivative of the general formula III in a suitable solvent and in the presence of an organic base preferably a primary or secondary amine. The process can carried by dissolving the aldehyde compound in a suitable solvent and an organic acid is added to the solution, then the dihydroimidazole compound is added to reaction mixture preferably dissolved in a suitable solvent and the mixture is under stirring for 1-12 hours, preferably for 1-6, more preferably 1-2 hours at elevated temperature between 60° C. and 120° C., preferably a 60° C. and 100° C., more preferably between 60° C. and 80° C., with the proviso that if the boiling point of the solvent is lower than 120° C., the reaction is kept on the boiling point of the solvent. In other words the reaction for the preparation of compound of general formula I according to according to the process of the present invention is carried out between preferably 40° C. and the boiling point the used solvent, preferably 60° C.-120° C.

The used aldehyde compounds and a large selection of similar compounds usually commercially available. Some exemplified aldehydes are not available, but we disclosed the suitable process for the preparation thereof in the experimental part of the description. Generally, the 2-methyl amino or hydroxy quinoline derivatives can be obtained according to well-known method by oxidization with selenium dioxide according to prior art. 2-methyl-quinoline compounds can also be prepared in well-known methods according to prior art. They can be achieved by a reaction of a suitable aniline derivative and crotonaldehyde. This reaction is known and part of the knowledge of the person skilled the art, even a new similar compound has to be prepared.

According to the present invention, the reaction of the compounds of the general formulas II and III can be carried out in different solvents. The reaction is can be carried out in several suitable solvent organic solvents e.g. organic acid, alcohol, dipolar aprotic solvent, ether type solvent, amid type solvent, nitril type solvent or sulfoxide type solvent or a mixture thereof, preferably in $C_1$-$C_4$ aliphatic acid solvent as acid solvent, $C_1$-$C_4$ alcohols as alcohols, amide solvents, nitrile solvents and sulfoxide solvents. More preferably the reaction can be carried out in acetic acid or propionic acid as acid solvent, tetrahydrofuran or dioxan as ether type solvent, formamide, dimethylformamide or diethyl formamide, n-methyl pyrrolidone as formamide, acetonitrile or propionitrile as nitrile type solvent, dimethyl sulfoxide, diethyl sulfoxide or sulfolane as sulfoxide type solvent.

The reaction between the compounds of general formula II and III is carried out in the presence of an organic base. As organic base primer or secondary amine, more preferably $C_1$-$C_4$ aliphatic amines or heterocyclic amines having one or more secondary or primary amino group can be used. Most preferably methylamine, ethylamine, propylamine, butylamine, dimethylamine, diethyl-amine, dipropyl-amine, di-butylamine or cyclic amines such as piperazine piperidine, pyrrolidine, morpholine can be used.

More particularly, the process can be carried out by dissolving the chosen aldehyde in N,N-dimethylformamide and the solution is added to 2 mL acetic acid. The chosen 3,5-dihydro-4H-imidazol-4-one (1 equivalent based on chosen aldehyde) is dissolved in N,N-dimethylformamide and added to the previous solution containing aldehyde. 0.02 mL of buthylamine was added. The resulting mixture is heated preferably to 80° C. for two hours, and the solvents are removed in vacuo. The resulting solid is dissolved in 10 ml mixture of methanol, acetonitrile and water 4:4:2, filtered and injected onto a preparative HPLC system. The mixture is eluted on a reverse phase C18 column with water (0.2% TFA)-acetonitrile (5%→95%) gradient. The pure fractions are concentrated to yield the product. Yields: 20-80%.

After the reaction, the products were purified by chromatography, when it was necessary. After the preparation of the product it can be transfer into salt or complex forms using the technics of the state of the art.

The compounds of the present invention are suitable for the use of imaging metal ions in solution, in biological samples, preferably cells, cell cultures, body tissues more preferably in living cells, in cell cultures, in body tissues. The use of these compounds is obvious based on the use of similar, but less effective compounds. These compounds of the general formula I does not requires any specific knowledge, skill or specific processes which would make more difficult the use these new compounds. The most important use of these compounds of the general formula I is imaging the concentration of metal ions especially $Zn^{2+}$ or $Ca^{2+}$ ions with laser microscope, preferably with one or multiphoton laser microscope, most preferably with two photon laser microscope.

The compounds of the present invention have several advantages which are very important in that field of the industry. First of all that these compounds have very strong complexes by using their 4-5 chelating hetero atoms which can provide stable and strong biding.

Advantages of compounds of the present invention can be seen evaluate the figures as follows:

The compounds of the present invention have very unexpected advantageous property for example.

The red shift of the emitted light for the compounds studied is important (higher wavelength, >500 nm) means deeper penetration into the tissue. The red shifted photon has lesser energy, which cause less significant damage in the cells or in the tissue upon the illumination. The red shifted excitation is more suitable for the two-photon imaging, because it is more accessible for the range of the pulse laser.

Larger Stokes shift (around 80-100 nm) is beneficial from the aspect of background emission, because the cross section of the excitation and emission bands are almost negligible. In this case the self-excitation is insignificant, so the emitted photon can be excluded from the excited photons.

On figure one the compound 28 of the present invention shows that the Fluorescent spectra of compound 28 in the presence of various Zn ion concentration. The maximum emitted wavelength is around 545 nm, reaching the red segment of the spectrum of the visible light. Furthermore on FIG. 2. The UV spectra of compound 28 is disclosed. The maximum wavelength is around 472 nm. In this case the Stokes shift is 73 nm, which is very advantageous for the in vitro microscopic study, due to the low cross section of the absorption and fluorescent. Similarly, also close the maximum (486 nm) in case of Compounds 32 (FIG. 3) and 33 (FIG. 4).

On FIG. 5 Fluorescent spectra of compound 29 in the presence of various Zn ion concentration (Zn-titration). The maximum emitted wavelength is around 520 nm. which also close to the visible light. This compound also shows the advantageous red shift effect which was discussed above. Although the UV spectra shows a maximum at 467 on FIG. 6, but it extends over 500 nm, ensuring a selective excitation.

Similarly, on FIG. 7 Fluorescent spectra of compound 31 in the presence of various Zn ion concentration (Zn-titration). The maximum emitted wavelength is around 545 nm, which reach the red area of the visible light spectra, so this compound also has a “red Shift” advantage. Its UV spectra on FIG. 8. shows the maximum wavelength is around 481 nm, but it extends over 500 nm.

Similarly, on FIGS. 9 and 10 the spectra also are evidence for the presence of advantageous effects of the compound 29. FIG. 9. Fluorescent spectra of compound 29 in the presence of various Zn ion concentration (Zn-titration). The maximum emitted wavelength is around 555 nm, which reach the red area of the visible light spectra. FIG. 10. The UV spectra of compound 30. The maximum wavelength is around 476 nm. but it extends over 500 nm.

UV spectra of compounds 34 (FIG. 11) and 35 (FIG. 12) also show that the maximum of these compounds are also almost 200 nm, and but it extends over 550 nm.

FIG. 13. The measured two-photon excitation scan spectrums of 29, 30 and 31 in the absence and presence of Zn-ion (0 mM and 1 mM, respectively). The spectrums were normalized based on the concentration of the sensors.

The three selected sensor compounds (29, 30, 31) were undertaken in two-photon suitability measurements. The same $Zn^{2+}$ free and 1 mM $Zn^{2+}$ containing stock solutions used for the determination of single photon photophysical properties were used in this case as well. Capillaries, applied for the 2P microscope, were charged into the solutions and filled, then the ends of the capillaries were sealed by immersion into hot wax. The capillaries were put onto a glass slide under the water-immersion lens of a two-photon microscope, then a droplet of water was carefully put onto above the capillary and the lens was immersed into a droplet. The top edge of the capillary was pulled into focus every time and then the focal point of the lens was shifted downwards with 50 mm to measure in the middle of the capillary. In these experiments, the excitation spectra were recorded, as the wavelength of the laser was changed from 700 up to 1040 and the intensity of the emitted light was detected. The filter used before the detector selected the photons between 450 and 600 nm. Images were recorded of the capillary in every nm step. The average brightness of the capillary was calculated and corrected with the brightness of the background.

The measured normalized excitation spectrums were normalized based on the concentration and plotted in FIG. 13. All the sensors in the absence of $Zn^{2+}$ did not emit detectable fluorescence. The fluorescence intensity increased dramatically in the presence of $Zn^{2+}$, proving their applicability of these compounds for 2P microscopy.

Furthermore, on FIGS. 14-17 four compounds are examined FIG. 15. The ion screening of compound 29. From left to right: Free (no ion), Zn2+, Ca2+, Mg2+, Na+, K+, Fe3+, Cu2+, Sn2+, Cd2+, Pb2+. This compound shows strong green fluorescence and strong selectivity towards Zn ion, exhibiting red-green light. The Zn/Ca fluorescence ratio is excellent, it can be use beside Ca-ion sensors. On FIG. 14. The ion screening of compound 30. This compound shows strong green fluorescence and strong selectivity towards Zn ion, exhibiting red-green light. It has lower intensity. On FIG. 16. The ion screening of compound 31. This compound shows strong green fluorescence and good selectivity towards Zn ion and weak against $Cd^{2+}$, exhibiting red-green light. The Zn/Ca fluorescence ratio is also good, it can be use beside Ca-ion sensors. On FIG. 17 is the ion screening of compound 33. As can be seen, this compound does not turn on in the presence of Zn2+, but the Ca2+ ion shows increased fluorescence intensity (it is less observable in this picture). Other ions also turn on the sensor, like Sn2+. So, it may sense these ions in the environmental samples.

A turned out that these compounds have good solubility and very sensitive and selective for Zn or some for Calcium, which very advantageous.

Further advantages of the compound of the present invention as follows:

These compounds have increased solubility compared to other compounds.

As small molecules they can be easy to prepare and they have high chemical and photo stability.

Further advantage that these compounds are solid and easily can be storage even long for time at room temperature.

Furthermore, these compounds have high photo absorption capacity, and their use is very advantageous for high 2P cross sections.

The compounds of the present invention have high Stokes shift (cca. 100 nm), red shifted emission and low background fluorescence.

From that point of view of Zn imaging is important, the large increase in fluorescence in the presence of Zn (>10×).

Furthermore, these compounds of the present invention work at low Zn concentration (100 um>10 nm) too.

Figure 1:
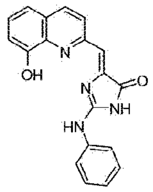
FIG. 1. Fluorescent spectra of compound 28 in the presence of various Zn ion concentration. The maximum emitted wavelength is around 545 nm, reaching the red segment of the spectrum of the visible light.
Figure 1:
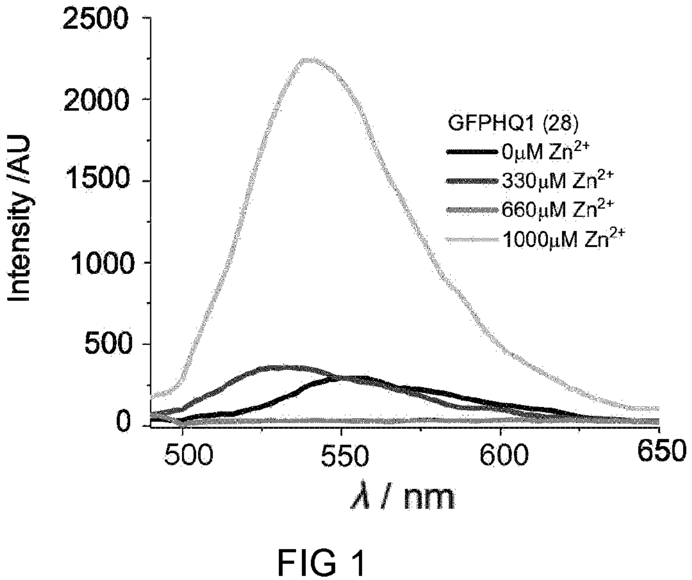

Our invention is demonstrated more particularly with examples below without limiting the scope of our invention to the examples:

Used Chemicals:

All chemicals and solvents used were purchased from Merck (Aldrich, Sigma-Aldrich) and Fluorochem in reagent grade. All chemicals were used without further purification. NMR solvents were from Eurisotop. HPLC solvents were purchased from Merck Thin layer chromatography (TLC) was performed on Kieselgel 60 $F_{254}$ plates from Merck and spots were visualized by UV light or by exposing it with iodine or the aqueous solution of 10% cerium (IV) sulphate, 10% ammonium molybdite and 15% sulfuric acid.

Precursors which are not commercially available are prepared with the process which is fully described in the relevant examples.

Used Analytical Procedures and Equipment's:

Reactions were routinely monitored by HPLC-MS or TLC. UV-VIS and MS were used as a detection method. Conditions of the measurements and parameters of the instrument:

Type: Shimadzu LCMS-2020 equipped with Shimadzu LC-20AD parallel pump, Shimadzu DG-20AS degasser, Shimadzu SIL-20A HT autosampler and a Shimadzu CTO-20A thermostat and a Shimadzu SPD-M20A 190-800 nm PDA detector. The used column was always Supelco 5 µm, 50×4.6 mm, C18 column thermostatic to 40° C. A 1:1 split was employed between the PDA and MS detectors. MS: ionisation: ESI 10000 V, $N_2$ flow 14 L/min, 250° C.

Two elution programs were used:

LCMS method A: gradient elution, flow rate 1 mL/min. Eluent A: 0.1% TFA in $H_2O$. Eluent B: 0.1% TFA in MCCN. Elution program: B concentration 0á100% linearly in 10 min.

LCMS method B: gradient elution, flow rate 1 ml/min. Eluent A: 10 g $NH_4HCO_3$ in 5 L $H_2O$. Eluent B: MCCN. Elution program: B concentration 0-100% linearly in 10 min.

In order to achieve the highest purity with the least effort, preparative HPLC purifications were employed. Parameters of the instrument:

Type: Armen Spot Prep II system. Column: Phenomenex, Gemini 250×50.00 mm; 10 µm, C18, 110 Å loading. Flow rate: 250 mL/min, 300 bar. Injection: manual, 10 mL loop. Detector: PDA, 4 ch., scan mode, 200-600 nm.

Gradient elution with unique gradient for each compounds were used. Two main methods were used based on the eluents:

method A: eluent A: 0.2% TFA in $H_2O$ áeluent B: MCCN method B: eluent A: 0.1% $NH_4HCO_3$ in $H_2O$ áeluent B: MeCN Column Chromatography for Purification:

Flash column chromatography was performed by an Interchim puriFlash® XS520Plus instrument used with dry loading (25 g RediSep Solid Load Cartridge) and Puriflash SILICA HP 15UM F0040 flash column using gradient elution in normal phase mode. Flow rate: 20 ml/min.

NMR Spectroscopy

NMR spectroscopy. NMR spectra were obtained on a Varian Unity INOVA spectrometer operating at an equivalent $^1H$ frequency of 400 or 500 MHz. Samples were prepared by dissolving 7-15 mg of the titled compounds in 750 µl of $CDCl_3$ or DMSO-d6. Notation for the $^1H$ NMR spectral splitting patterns includes singlet (s), doublet (d), triplet (t), broad (br) and multiplet/overlapping peaks (m). Signals are given as δ values in ppm, coupling constants (J) are expressed in Hertz.

Microwave Reactor

A CEM Discover System 908005 MW reactor was used.

Methods and Materials Used in the Analytical Experiments.

Fluorescent spectra were recorded on an FLS920 Fluorescence Spectrometer from Edinburgh Instrument. A quartz cuvette with 3 mL volume and 1 cm length was used. Absorption spectra were recorded on a ThermoFisher NanoDrop 1000 Spectrophotometer. The two-photon measurements were performed on the custom Femtonics Dobos Dual system using a water immersion lens, a Mai Tai High-Power laser operated at 50 mW. For processing the images, ImageJ software was used.

PREPARATIVE EXAMPLES

Example 1

General Procedure for Preparation of General Formula I

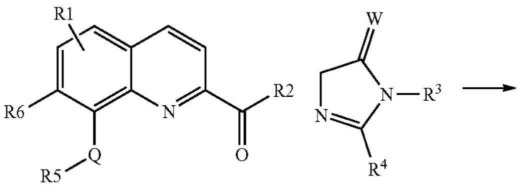

II III

-continued

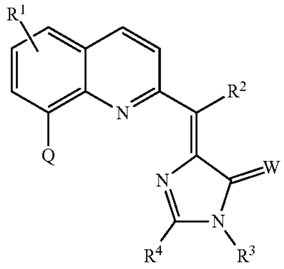

I

Quinoline-2-carbaldehyde (1 mmol) was dissolved in 5 mL NN-dimethylformamide and the solution is added to 2 mL acetic acid. 3,5-Dihydro-4H-imidazol-4-one (1 eq., 1 mmol) is dissolved in 5 mL NN-dimethylformamide and added to the previous solution. 0.020 mL of butylamine was added to the mixture, which was stirred at 80° C. for two hours. The solvents are removed in vacuo. The resulting solid is dissolved in 10 mL of the mixture of methanol, acetonitrile and water 4:4:2, the solid precipitates removed by filtration, the liquid phase was injected onto a preparative HPLC system. The mixture is eluted on a reverse phase $C_{18}$ column with water (0.2% TFA)-acetonitrile (5% á 95%) gradient. The pure fractions were collected and concentrated to yield the desired product. Yields: 20-80%.

Example 2

Preparation of (Z)-5-((8-hydroxyquinolin-2-yl)methylene)-2-(phenylamino)-3,5-dihydro-4H-imidazol-4-one (28)

28

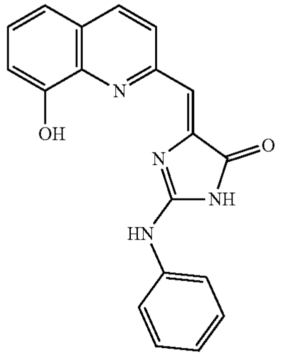

Titled compound is prepared according to general procedure of Example 1 with the proviso that the used aldehyde was 8-hydroxy-2-quinolinecarboxaldehyde (14510-06-6) and the used imidazole was 2-(phenylamino)-3,5-dihydro-4H-imidazol-4-one.

Yield: 68%

Product: Bright orange powder. Soluble in alcohols, DMSO, moderately soluble in water. The aqueous solution is orange and emits no fluorescence. Upon addition of aqueous 1 mM $ZnCl_2$ the colour changes to yellow and the solution emits fluorescence upon irradiation.

$^1H$ NMR (400 MHz, DMSO-$d_6$) δ 11.46 (s, 1H), 8.69 (s, 1H), 8.05 (s, 1H), 7.89-7.41 (m, 6H), 7.36 (s, 1H), 7.20 (t, J=7.4 Hz, 1H), 6.68 (s, 1H).

FIG. 1. Fluorescence spectra of compound 28 pH 7.4 (0.1 M) HEPES buffer containing different amounts of $Zn^{2+}$. Values are not normalized, spectra were recorded at the maximum excitation wavelength.

Figure 2:
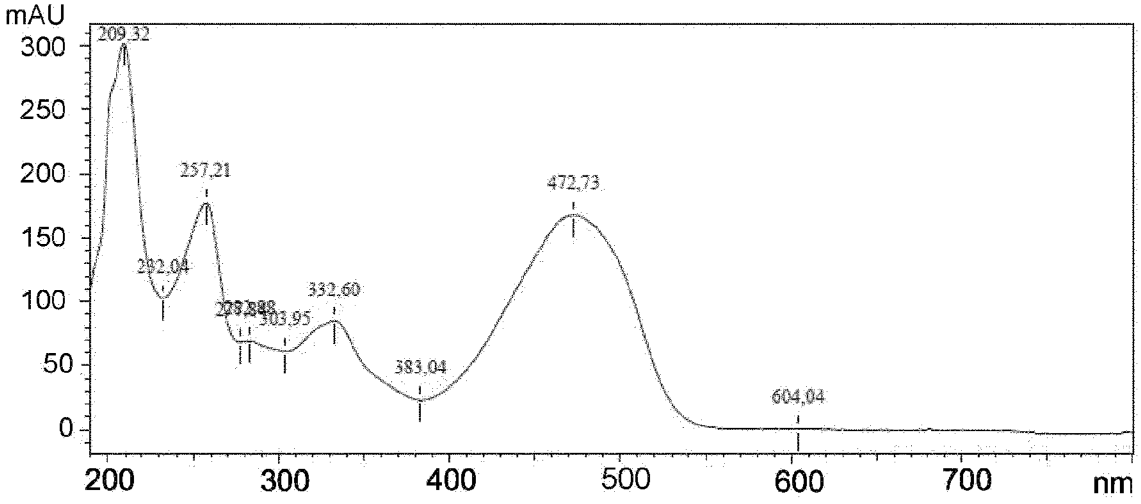
FIG. 2. The UV spectra of compound 28. The maximum wavelength is around 472 nm. In this case the Stokes shift is 73 nm, which is very advantageous for the in vitro microscopic study, due to the low cross section of the absorption and fluorescent.

FIG. 2. Fluorescence spectra of compound 28

Example 3

Preparation of (Z)-5-((8-methoxyquinolin-2-yl) methylene)-2-(phenylamino)-3,5-dihydro-4H-imidazol-4-onen (32)

32

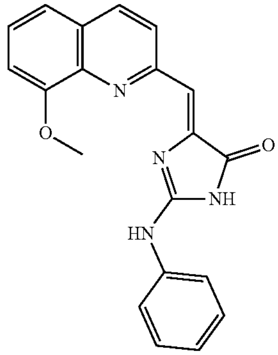

Titled compound is prepared according to general procedure of Example 1 with the proviso that the used aldehyde was 8-methoxy-2-quinolinecarbaldehyde (103854-64-4) and the used imidazole was 2-(phenylamino)-3,5-dihydro-4H-imidazol-4-one.

Yield: 25%

Product: Bright orange powder. Soluble in alcohols, DMSO, moderately soluble in water. The aqueous solution is orange and emits no fluorescence. Upon addition of aqueous 1 mM $ZnCl_2$ the colour changes to green and the solution emits fluorescence upon irradiation.

Figure 3:
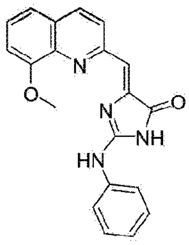
FIG. 3. The UV spectra of compound 32. The maximum wavelength is around 486 nm.
Figure 3:
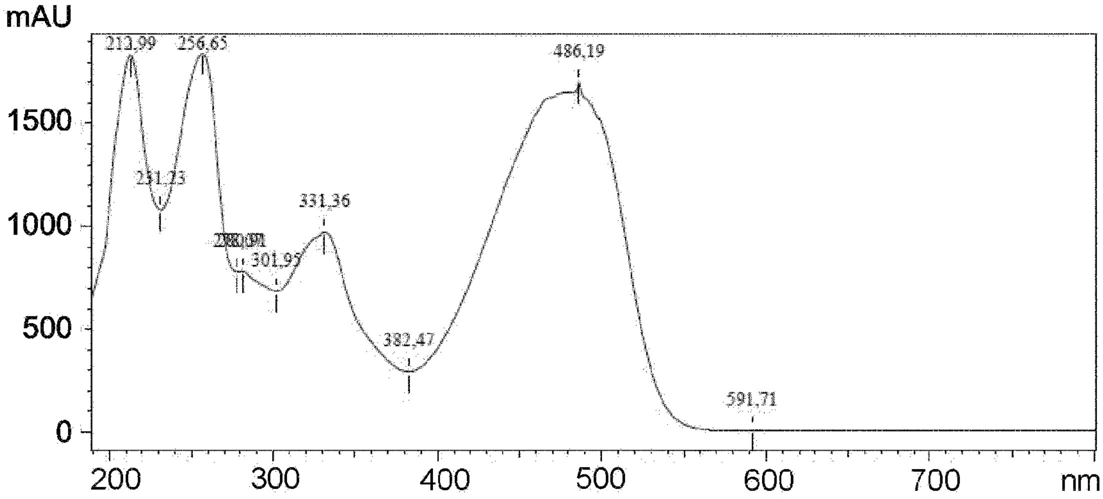

FIG. 3. UV-VIS spectra of the compound of 32

Example 4

Preparation of (Z)-5-((8-(dimethylamino)quinolin-2-yl)methylene)-2-(phenylamino)-3,5-dihydro-4H-imidazol-4-one (29)

29

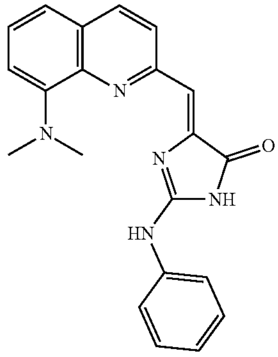

Titled compound is prepared according to general procedure of Example 1 with the proviso that the used aldehyde was 8-(dimethylamino)quinoline-2-carbaldehyde (1415217-83-2) and the used imidazole was 2-(phenylamino)-3,5-dihydro-4H-imidazol-4-one.

Yield: 90%

Product: Red powder. Soluble in alcohols, DMSO, water. The aqueous solution is reddish and emits no fluorescence. Upon addition of aqueous 1 mM $ZnCl_2$ the colour changes to greenish and the solution emits fluorescence upon irradiation.

$^1H$ NMR (400 MHz, DMSO-$d_6$) δ 8.61 (d, J=8.6 Hz, 1H), 8.40 (s, 1H), 7.89 (d, J=8.0 Hz, 1H), 7.80 (s, 1H), 7.67 (t, J=7.9 Hz, 1H), 7.61 (s, 1H), 7.46 (t, J=7.9 Hz, 2H), 7.23 (t, J=7.4 Hz, 1H), 6.75 (s, 1H), 3.01 (s, 6H).

Figure 5:
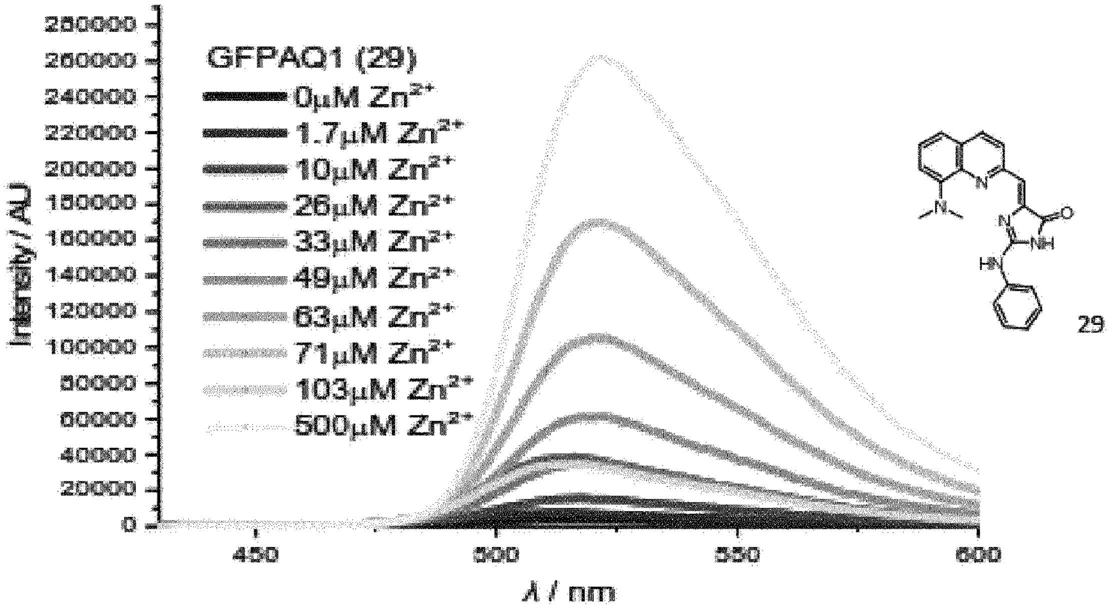
FIG. 5. Fluorescent spectra of compound 29 in the presence of various Zn ion concentration (Zn-titration). The maximum emitted wavelength is around 520 nm.

FIG. 5. Fluorescence spectra of the compound of 29 in 0.1 M HEPES buffer (pH 7.4) containing different amounts of $Zn^{2+}$.

Figure 6:
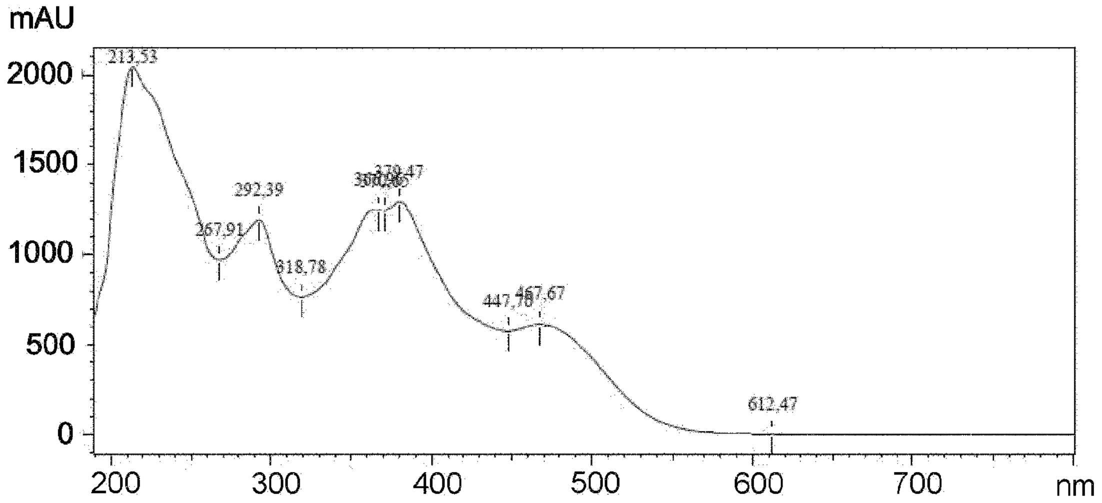
FIG. 6. The UV spectra of compound 29. The maximum wavelength is around 467 nm, but it extends over 500 nm, ensuring a selective excitation.

FIG. 6. UV-VIS spectra of the compound of 29.

Example 4/A

Preparation of 8-(dimethylamino)quinoline-2-carbaldehyde precursor 190 mg (1.7 mmol, 1.3 eq.) of selenium dioxide was suspended in 10 ml dioxane and 0.1 ml $H_2O$. The mixture was stirred heated to 80° C. and 250 mg (1.34 mmol, 1 eq.) of N,N,2-trimethylquinolin-8-amine was added. After 3 hours, the reaction was completed and the mixture was cooled, filtered through a pad of celite eluted with dioxane and the solvents were evaporated under reduced pressure. Flash chromatography on silica gel was performed. (dichloromethane/cyclohexane 1:1). The pure fractions were collected, and solvents were removed by vacuo.

Example 4/B

Preparation of NN, 2-trimethylquinolin-8-amine Precursor 500 mg (3.65 mmol, 1 eq.) of 2-(N,N-dimethylamino)-aniline (38) was dissolved in 6M HCl (6.6 mL), 510 mg of crotonaldehyde (39) (7.3 mmol, 2 eq., mixture of E and Z isomers) in toluene (5 mL) was added. After stirring at RT for 1 hour, 5 mL of toluene was added and the mixture was refluxed for 4 hours. The mixture was cooled, and the organic layer was removed. NaOH was added to the aqueous phase until the pH was 7, then the mixture was extracted with dichloromethane (3×20 mL). The combined organic phase was dried over anhydrous magnesium sulphate, and the solvent was evaporated under reduced pressure. This residue (4.00 g) was purified by flash chromatography (eluent dichloromethane/cyclohexane 1/1).[1]

Yield: 97%

Example 5

Preparation of (Z)-5-((8-(methyl(pyridin-2-ylmethyl)amino)quinolin-2-yl)methylene)-2-(phenylamino)-3,5-dihydro-4H-imidazol-4-one (31)

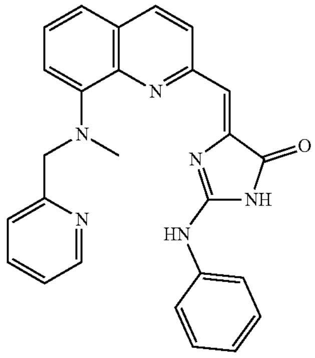 [SMILES: CN(Cc1ccccn1)c1cccc2ccc(/C=C3\N=C(Nc4ccccc4)NC3=O)nc12]

Titled compound was prepared according to general procedure of Example 1 with the proviso that the used aldehyde: 8-(methyl(pyridin-2-ylmethyl)amino)quinoline-2-carbaldehyde was and the used imidazole was 2-(phenylamino)-3,5-dihydro-4H-imidazol-4-one Yield: 90%

Product: Orange powder. Soluble in alcohols, DMSO, moderately soluble in water. The aqueous solution is reddish and emits no fluorescence. Upon addition of aqueous 1 mM $ZnCl_2$ the colour changes to yellow and the solution emits fluorescence upon irradiation.

$^1H$ NMR (400 MHz, DMSO-$d_6$) δ 11.16 (s, 1H), 8.72 (d, J=4.8 Hz, 1H), 8.52 (bs, 1H), 8.47 (d, J=8.4 Hz, 1H), 8.17 (s, 1H), 7.70-7.58 (m, 4H), 7.52 (dt, J=15.4, 7.6 Hz, 2H), 7.41 (t, J=7.9 Hz, 2H), 7.29 (d, J=7.0 Hz, 1H), 7.15 (t, J=7.4 Hz, 1H), 6.15 (s, 1H), 4.77 (s, 2H), 2.93 (s, 3H).

$^{13}C$ NMR (101 MHz, DMSO-$d_6$) δ 158.59, 158.26, 157.37, 151.82, 146.09, 139.25, 138.43, 129.16, 127.64, 127.15, 123.93, 123.86, 122.41, 120.77, 120.55, 117.23, 59.44, 40.56.

Figure 7:
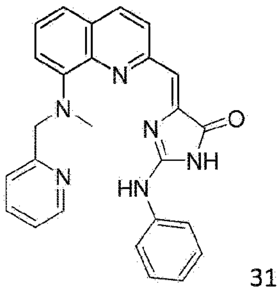
FIG. 7. Fluorescent spectra of compound 31 in the presence of various Zn ion concentration (Zn-titration). The maximum emitted wavelength is around 545 nm, which reach the red area of the visible light spectra.
Figure 7:
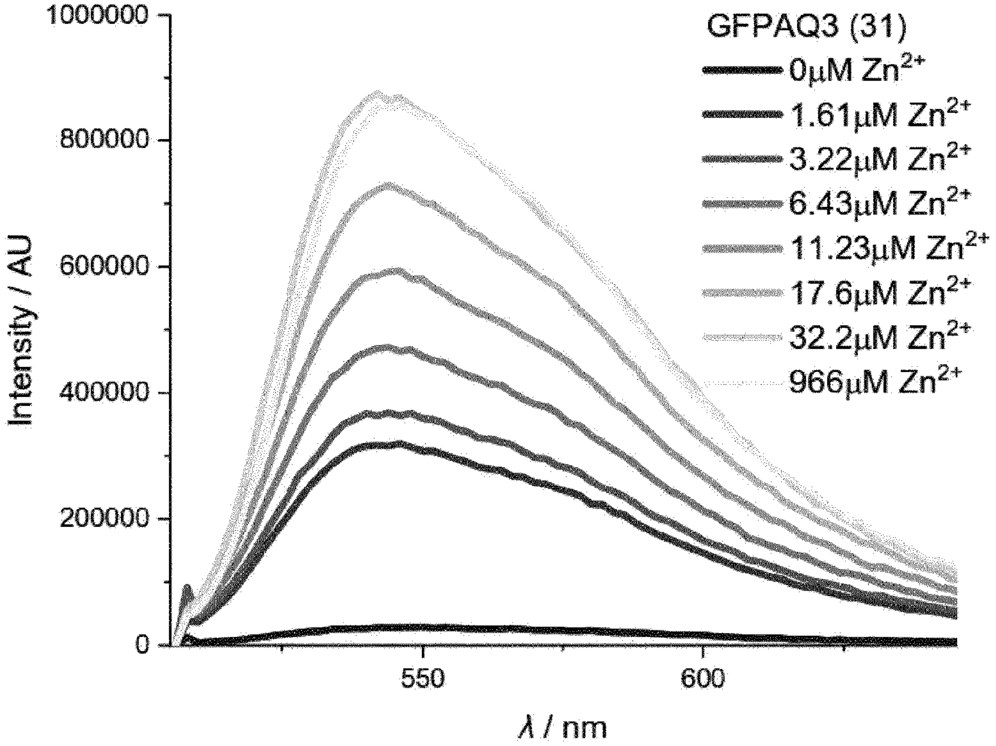

FIG. 7. Fluorescence spectra of the compound of 31 in pH 7.4 (0.1 M) HEPES buffer containing different amounts of $Zn^{2+}$.

Figure 8:
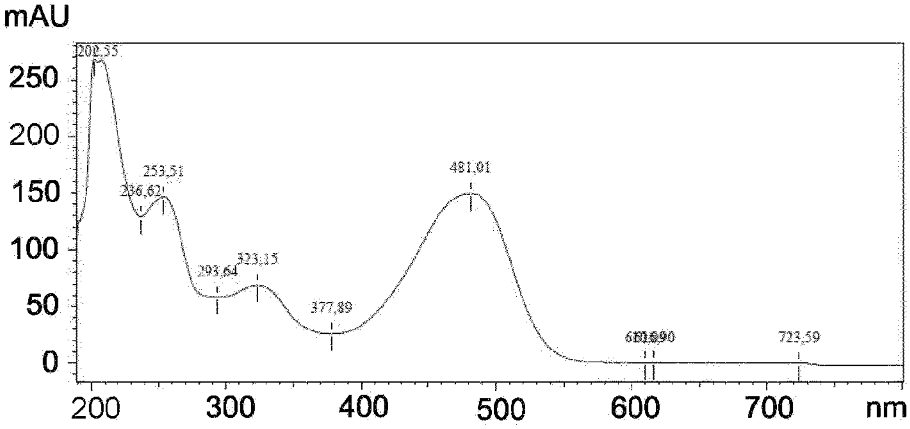
FIG. 8. The UV spectra of compound 31. The maximum wavelength is around 481 nm, it extends over 500 nm.

FIG. 8. UV-VIS spectra of the compound of 31.

Example 5/A

Preparation of 8-(methyl(pyridin-2-ylmethyl)amino)quinoline-2-carbaldehyde Precursor 121 mg (1.09 mmol, 1.3 eq.) of selenium dioxide was suspended in 5 mL dioxane and 0.1 mL $H_2O$. The mixture was stirred at 80° C. and 232 mg (0.80 mmol, 1 eq.) of N,2-dimethyl-N-(pyridin-2-ylmethyl)quinolin-8-amine was added. After 3 hours, the mixture was filtered through celite and was washed with dichloromethane. Solvents were removed in vacuo, and the crude product was purified by column chromatography on silica gel. (Hex/EtOAc/7M $NH_3$ in MeOH 7/1/0.5).[1]

Yield: 85%

Example 5/B

Preparation of N,2-dimethyl-N-(pyridin-2-ylmethyl)quinolin-8-amine Precursor

In a 10 mL microwave pressure vial 333 mg (1.5 mmol, 1.25 eq.) 8-bromo-2-methylquinoline was dissolved in 5 mL toluene. 140 μL (147 mg, 1.20 mmol, 1 eq.) 2(methylamino)pyridine, 216 mg (2.25 mmol, 1.9 eq.) NaOtBu, 47 mg (0.08 mmol, 0.05 eq.) rac-BINAP, 28 mg $Pddba_2$ (0.05 mmol, 0.04 eq.) were added. The vial was flushed with argon and capped. The mixture was heated to 120° C. by MW and was irradiated and stirred for 4 hours at 120° C. After cooling, the mixture was diluted with dichloromethane (15 mL) and water (15 mL) and the aqueous phase was extracted with dichloromethane (2×15 mL) The combined organic phases were dried over anhydrous $MgSO_4$ and concentrated. The crude product was purified by flash chromatography (using eluent Hex/EtOAc 4/1 and a few drops of aqueous 7M $NH_3$ (competing base) EtOAc/MeOH 9/1).[1]

Yield: 85%

Example 6

Preparation of (Z)-5-((8-((2-(dimethylamino)ethyl)(methyl)amino)quinolin-2-yl)methylene)-2-(phenylamino)-3,5-dihydro-4H-imidazol-4-one

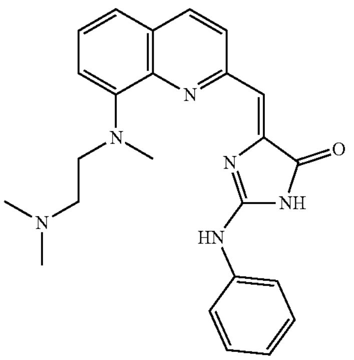

Titled compound is prepared according to general procedure of Example 1 with the proviso that the used aldehyde: 8-((2-(dimethylamino)ethyl)(methyl)amino)quinoline-2-carbaldehyde was and the used imidazole was 2-(phenylamino)-3,5-dihydro-4H-imidazol-4-one Yield: 33%

Product: Brown powder. Soluble in alcohols, DMSO, moderately soluble in water. The aqueous solution is orange and emits no fluorescence. Upon addition of aqueous 1 mM $ZnCl_2$ the colour gets brighter and the solution emits fluorescence upon irradiation.

Figure 9:
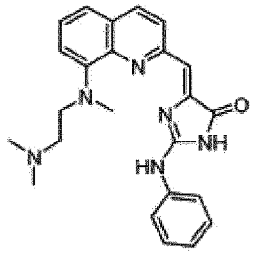
FIG. 9. Fluorescent spectra of compound 30 in the presence of various Zn ion concentration (Zn-titration). The maximum emitted wavelength is around 555 nm, which reach the red area of the visible light spectra.
Figure 9:
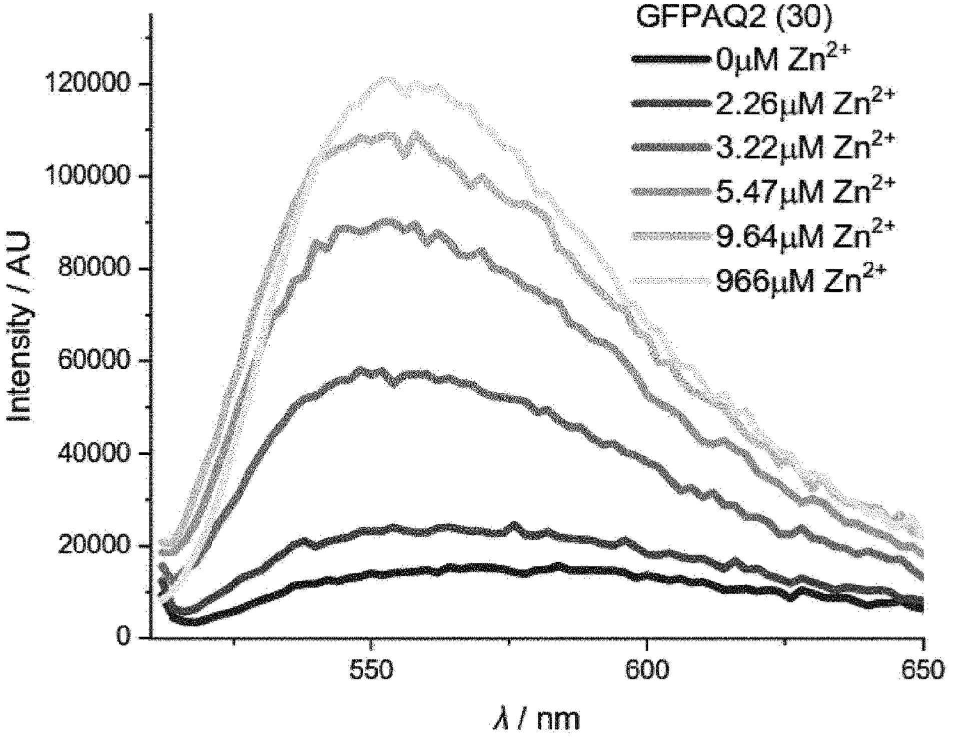

FIG. 9. Fluorescence spectra of the compound of 30 in pH 7.4 (0.1 M) HEPES buffer containing different amounts of $Zn^{2+}$ ion.

Figure 10:
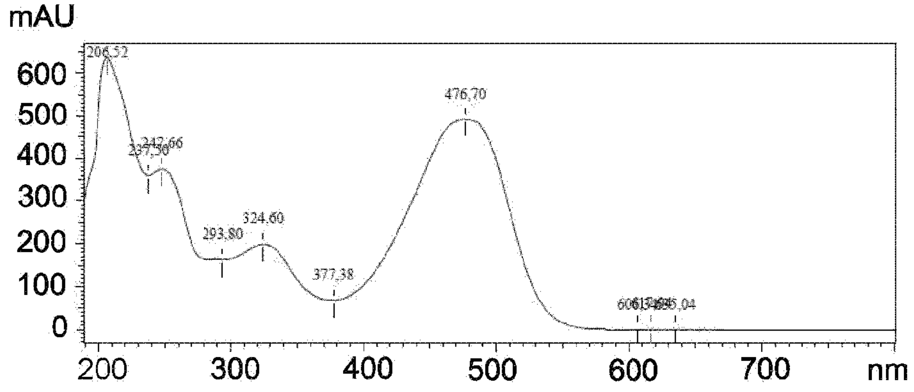
FIG. 10. The UV spectra of compound 30. The maximum wavelength is around 476 nm.
Figure 11:
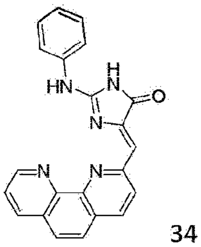
FIG. 11. The UV spectra of compound 34. The maximum wavelength is around 498 nm, exhibiting a red (highest wavelength) excitation.
Figure 11:
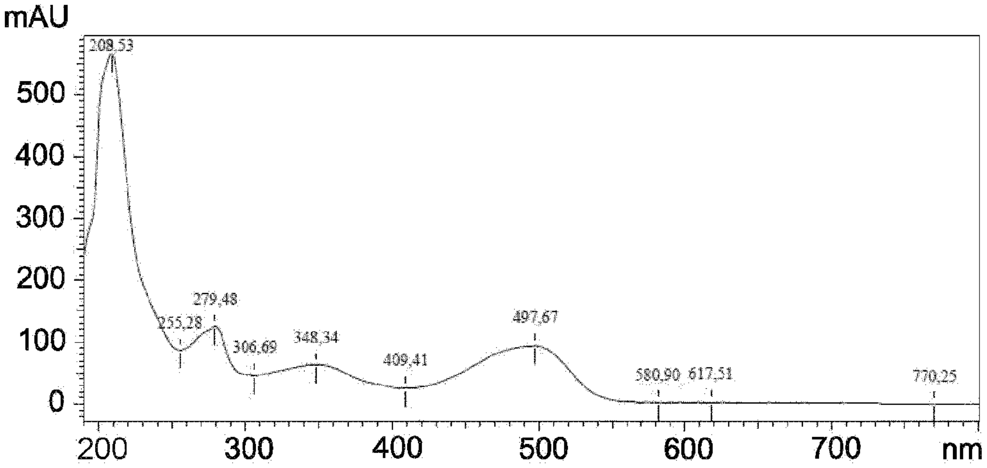
Figure 12:
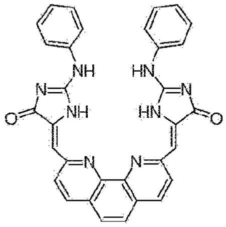
FIG. 12. The UV spectra of compound 35. The maximum wavelength is at 513 nm, exhibiting the reddest (highest wavelength) excitation in the series FIG. 13. The measured two-photon excitation scan spectrums of 29, 30 and 31 in the absence and presence of Zn-ion (0 mM and 1 mM, respectively). The spectrums were normalized based on the concentration of the sensors.
Figure 12:
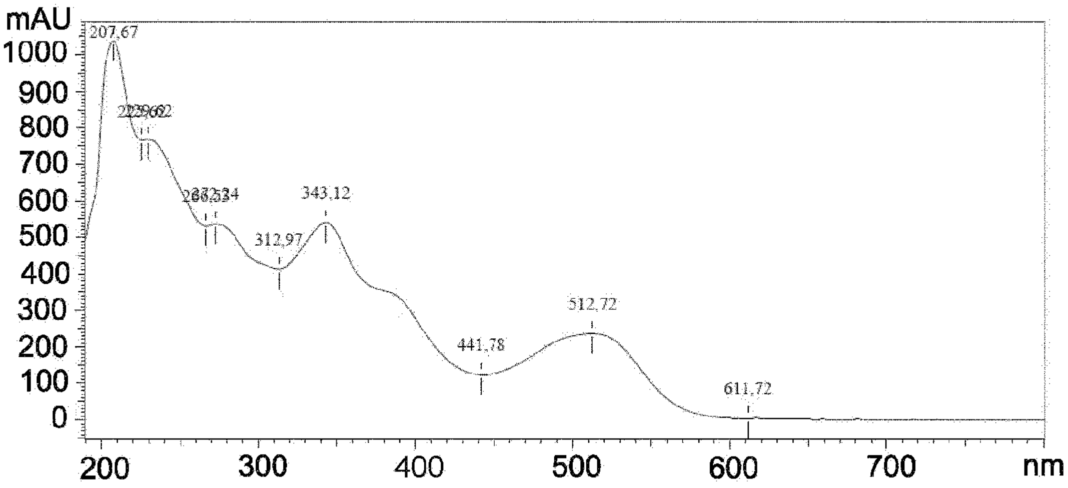

FIG. 10. UV-VIS spectra of the compound of 30.

Example 6/A

Preparation of 8-((2-(dimethylamino)ethyl)(methyl)amino)quinoline-2-carbaldehyde Precursor 160 mg (1.44 mmol, 1.3 eq.) of selenium dioxide was suspended in 10 mL dioxane and 0.1 mL $H_2O$. The mixture was stirred at 80° C. and 270 mg (1.11 mmol, 1 eq.) of N1,N1,N2-trimethyl-N2-(2-methylquinolin-8-yl)ethane-1,2-diamine was added. After 1 hour, the solvents were evaporated, the mixture was eluted on an alumina column with 5 CV dichloromethane/MeOH 4:1. After removing the solvents, the residue was concentrated and dissolved in a 10 mL mixture of methanol, acetonitrile and water 4:4:2, then injected onto prep. HPLC (previously described method). Pure fractions were collected, then acetonitrile was evaporated and the aqueous residue was lyophilized after freezing.[1]

Yield: 15%

Example 6/B

Preparation of $N_1$,$N_1$,$N_2$-trimethyl-$N_2$-(2-methylquinolin-8-yl)ethane-1,2-diamine Precursor In a 10 mL microwave pressure vial 500 mg (2.251 mmol, 1 eq.) 8-bromo-2-methylquinoline was dissolved in 7.5 ml toluene. 440 μl (344 mg, 3.38 mmol, 1.5 eq.) $N_1$,$N_1$,$N_2$-trimethylethane-1,2-diamine, then 320 mg (3.38 mmol, 1.5 eq.) NaOtBu, 70 mg (0.11 mmol, 0.05 eq.) rac-BINAP, palladium(0) bis(dibenzylideneacetone) (0.09 mmol, 0.04 eq.) were added. The vial was flushed with argon and capped. The mixture was heated to 120° C. by MW and was irradiated and stirred for 4 hours. The mixture was concentrated then eluted on an alumina column using dichloromethane/MeOH 3:2 eluent to give the desired product.

Yield: 60%

Example 7

Preparation of (Z)-2,2'-((2-((5-oxo-2-(phenylamino)-1,5-dihydro-4H-imidazol-4-ylidene)methyl)quinolin-8-yl)azanediyl)diacetic acid (33)

33

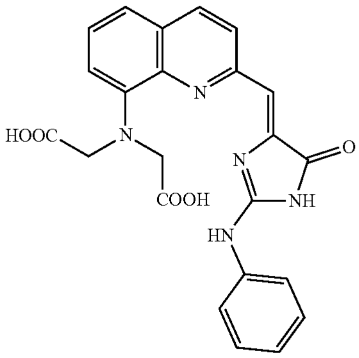

Titled compound is prepared according to general procedure of Example 1 with the proviso that the used aldehyde: diethyl 2,2'-((2-formylquinolin-8-yl)azanediyl)diacetate was and the used imidazole was 2-(phenylamino)-3,5-dihydro-4H-imidazol-4-one. The intermediate diester product was isolated in 28% yield which was dissolved in ethanol, and 10 eq. 20% NaOH solution was added. After stirring for one hour, the solution was purified by preparative HPLC using the method described in the general procedure. Yield: 95%

Figure 4:
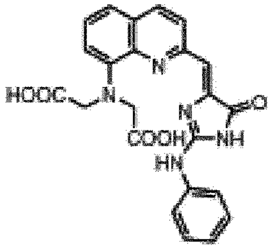
FIG. 4. The UV spectra of compound 33. The maximum wavelength is around 486 nm.
Figure 4:
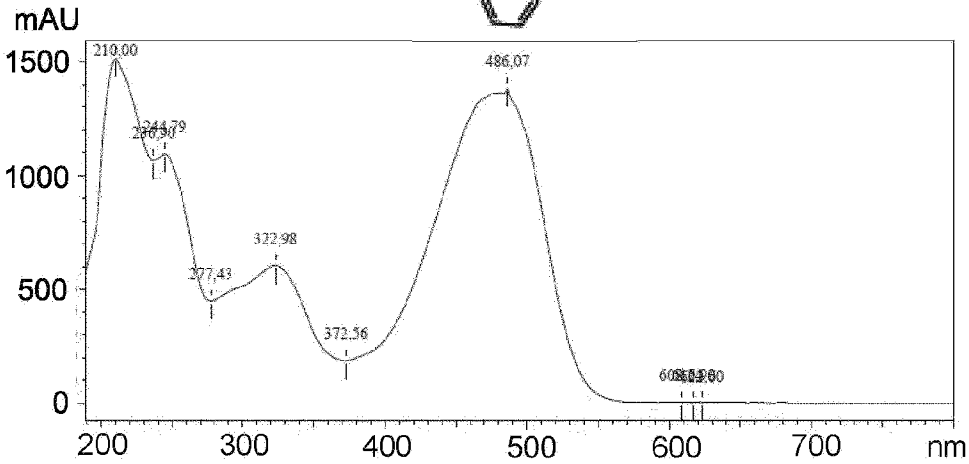

FIG. 4. Fluorescence spectra of 33

Example 7/A

Procedure for the preparation of precursor diethyl 2,2'-((2-formylquinolin-8-yl)azanediyl)diacetate 197 mg (1.77 mmol, 1.3 eq.) of selenium dioxide was suspended in 10 mL dioxane and 0.1 mL $H_2O$. The mixture was stirred at 80° C. and 45 mg (1.36 mmol, 1 eq.) of diethyl 2,2'-((2-methylquinolin-8-yl)azanediyl)diacetate was added. After 10 hours, the reaction mixture was filtered through a pad of celite, concentrated, then purified with preparative HPLC using the method described before.[1]

Yield: 66%

Example 7/B

Procedure for the preparation of precursor diethyl 2,2'-((2-methylquinolin-8-yl)azanediyl)diacetate 1.0 g (6.33 mmol, 1 eq.) 8-aminoquinaldine was dissolved in 5 mL acetonitrile, and 1.53 mL (2.31 g, 13.93 mmol, 2.2 eq.) of ethyl-bromoacetate was added to the mixture. After 3 hours, the reaction mixture was concentrated. The crude residue was dissolved in 50 mL dichloromethane and extracted with water (3×50 mL), than brine (3×30 mL). The organic layer was dried over $MgSO_4$ and concentrated. Purification was carried out by chromatography on silica gel. Elution with Hexane/EtOAc 9:1 removes impurities, then the product was eluted with pure EtOAc.

Yield: 45%.

Example 8

Process for preparation of (Z)-5-((1,10-phenanthrolin-2-yl)methylene)-2-(phenylamino)-3,5-dihydro-4H-imidazol-4-one (34)

34

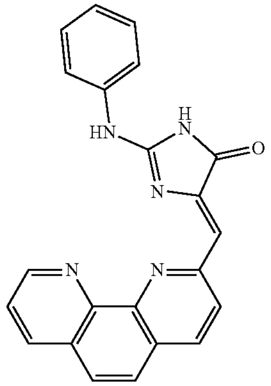

Titled compound is prepared according to general procedure of Example 1 with the proviso that the used aldehyde is 1,10-Phenanthroline-2-carbaldehyde (33795-37-8) and the used imidazole was 2-(phenylamino)-3,5-dihydro-4H-imidazol-4-one.

Yield: 21%

Product: Brick red coloured powder. Moderately soluble in THF, soluble in DMSO, soluble in the mixture of DMSO and water.

Example 8

Process for Preparation of (5Z,5'Z)-5,5'-((1,10-phenanthroline-2,9-diyl)bis(methanylylidene))bis(2-(phenylamino)-1,5-dihydro-4H-imidazol-4-one) (35)

35

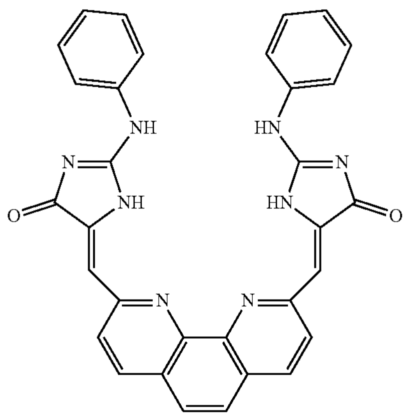

Titled compound is prepared according to general procedure* of Example 1 with the proviso that the used aldehyde was 1,10-Phenanthroline-2,9-dicarbaldehyde (57709-62-3) and the used imidazole was 2-(phenylamino)-3,5-dihydro-4H-imidazol-4-one.

*The general procedure is modified: 2.1 eq. of the aldehyde was used.

Yield: 33%

Product: Brick red coloured powder. Moderately soluble in THF, soluble in DMSO, soluble in the mixture of DMSO and water.

Example 8

The measured two-photon excitation scan spectrums of 29, 30 and 31 in the absence and presence of Zn-ion (0 mM and 1 mM, respectively). The spectrums were normalized based on the concentration of the sensors.

The three selected sensor compounds (29, 30, 31) were undertaken in two-photon suitability measurements. The same $Zn^{2+}$ free and 1 mM $Zn^{2+}$ containing stock solutions used for the determination of single photon photophysical properties were used in this case as well. Capillaries, applied for the 2P microscope, were charged into the solutions and filled, then the ends of the capillaries were sealed by immersion into hot wax. The capillaries were put onto a glass slide under the water-immersion lens of a two-photon microscope, then a droplet of water was carefully put onto above the capillary and the lens was immersed into a droplet. The top edge of the capillary was pulled into focus every time and then the focal point of the lens was shifted downwards with 50 mm to measure in the middle of the capillary. In these experiments, the excitation spectra were recorded, as the wavelength of the laser was changed from 700 up to 1040 and the intensity of the emitted light was detected. The filter used before the detector selected the photons between 450 and 600 nm. Images were recorded of the capillary in every nm step. The average brightness of the capillary was calculated and corrected with the brightness of the background.

Figure 13:
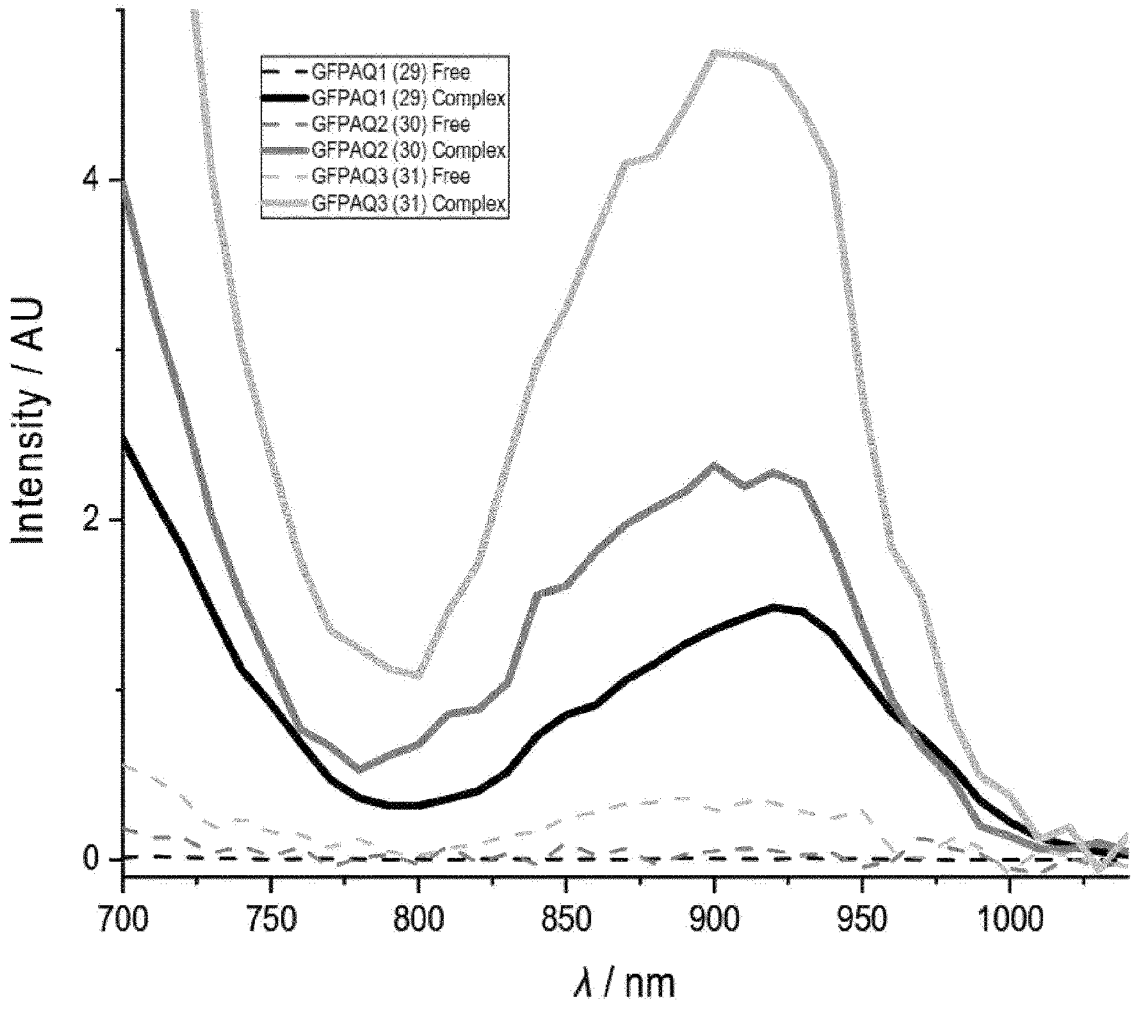
Figure 14:
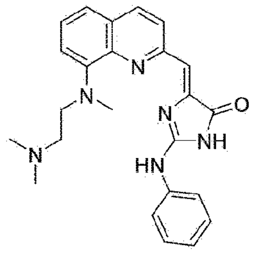
FIG. 14. The ion screening of compound 30. From left to right: Free (no ion), Zn2+, Ca2+, Mg2+, Na+, K+, Fe3+, Cu2+, Sn2+, Cd2+, Pb2+. This compound shows strong green fluorescence and strong selectivity towards Zn ion, exhibiting red-green light. It has lower intensity.
Figure 14:
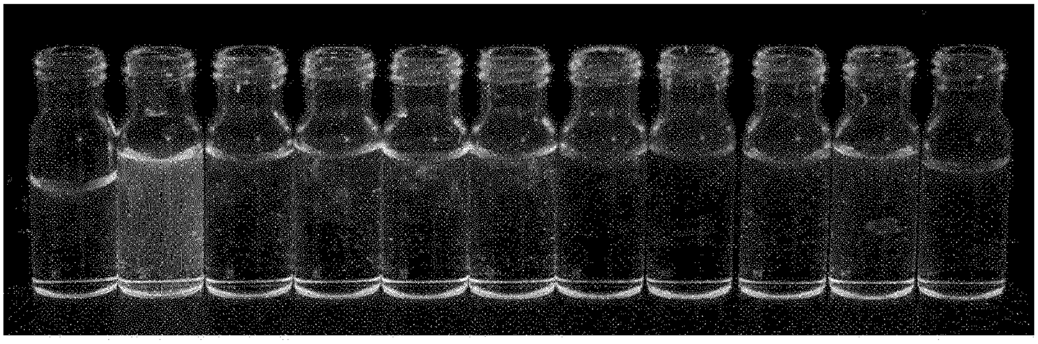
Figure 15:
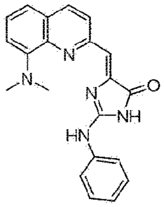
FIG. 15. The ion screening of compound 29. From left to right: Free (no ion), Zn2+, Ca2+, Mg2+, Na+, K+, Fe3+, Cu2+, Sn2+, Cd2+, Pb2+. This compound shows strong green fluorescence and strong selectivity towards Zn ion, exhibiting red-green light. The Zn/Ca fluorescence ratio is excellent, it can be use beside Ca-ion sensors.
Figure 15:
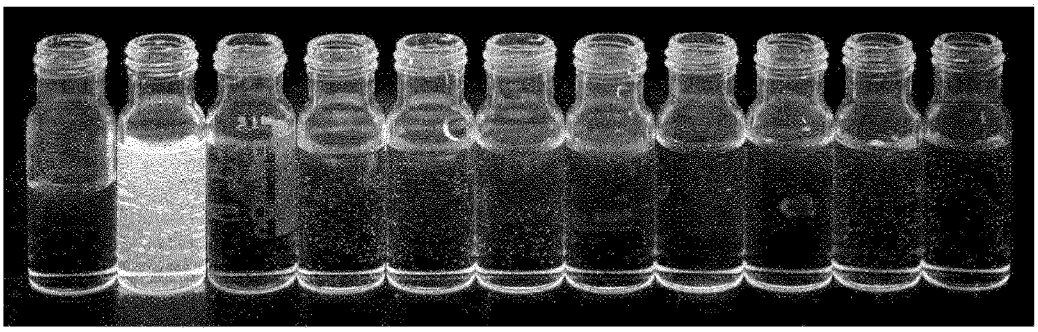
Figure 16:
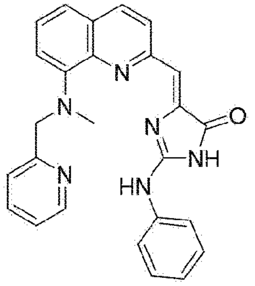
FIG. 16. The ion screening of compound 31. From left to right: Free (no ion), Zn2+, Ca2+, Mg2+, Na+, K+, Fe3+, Cu2+, Sn2+, Cd2+, Pb2+. This compound shows strong green fluorescence and good selectivity towards Zn ion and weak against Cd2+, exhibiting red-green light. The Zn/Ca fluorescence ratio is also good, it can be use beside Ca-ion sensors.
Figure 16:
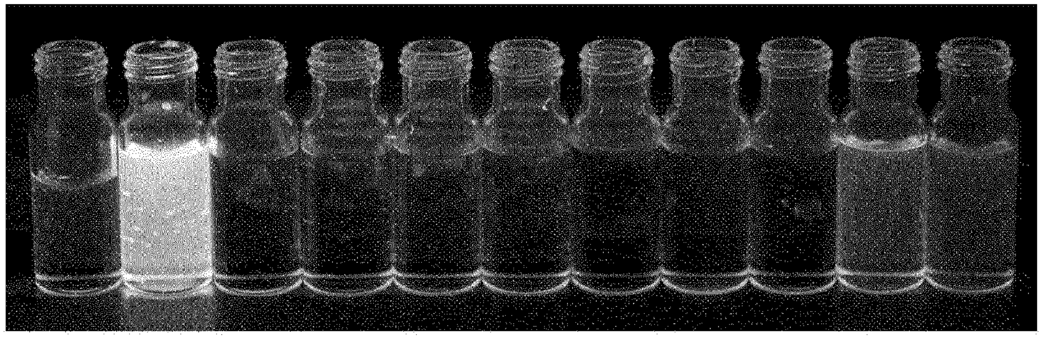
Figure 17:
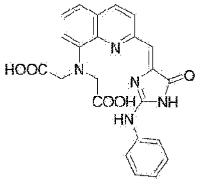
FIG. 17. The ion screening of compound 33. From left to right: Free (no ion), Zn2+, Ca2+, Mg2+, Na+, K+, Fe3+, Cu2+, Sn2+, Cd2+, Pb2+. As can be seen, this compound does not turn on in the presence of Zn2+, but the Ca2+ ion shows increased fluorescence intensity (it is less observable in this picture). Other ions also turn on the sensor, like Sn2+. So, it may sense these ions in the environmental samples.
Figure 17:
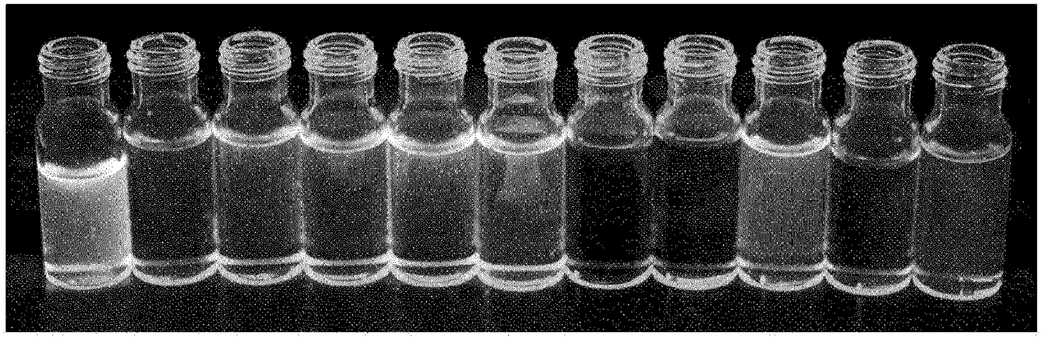

The measured normalized excitation spectrums were normalized based on the concentration and plotted in FIG. 13.

All the sensors in the absence of $Zn^{2+}$ did not emit detectable fluorescence. The fluorescence intensity increased dramatically in the presence of $Zn^{2+}$, proving their applicability of these compounds for 2P microscopy.

The invention claimed is:

1. A compound of formula I

I

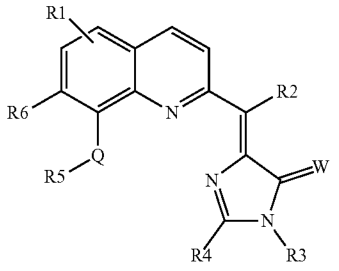

wherein

Q stands for —O—$R^5$ or —$NR^5R^9$ group,

W stands for an O or S atom, $R^1$, $R^2$, $R^3$ and $R^6$ stands for a H atom, $R^4$ stands for an —O-alkyl, —NH-alkyl, —NH-aryl group, $R^5$, $R^9$, independently stand for a H atom or alkyl, Me, Et, cyclohexyl, —$CH_2$—$CH_2$—$NMe_2$, —$CH_2$—$CH_2$—N($CH_2Pyr)_2$, carboxymethyl group, aryl group, or $R^5$ and $R^6$ form a heterocyclic ring, or $R^5$ and $R^9$ form a double bond connected to an alkyl group, or form a heterocyclic ring with the group $R^6$, or a salt or complex thereof.

2. A salt of the compound of formula I according to claim 1, wherein the salt forming compound is a.) an organic acidic compound, b.) a monovalent or polyvalent inorganic acid, c.) an organic and inorganic base.

3. A metal complex, which is the compound according to claim 1 in a complex with a $Zn^{2+}$ ion.

4. A process for preparing the compound of formula I according to claim 1, or a salt or a complex thereof, comprising reacting a compound of formula II

II

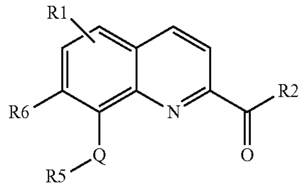

wherein:

Q, $R^1$, $R^2$, $R^5$ and $R^6$ are defined as for the compound of formula I, with a compound of formula III

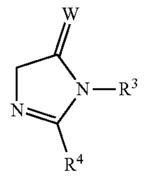

wherein:

W, $R^3$ and $R^4$ are defined as for the compound of formula I, then the obtained compound of formula I is optionally isolated, or optionally with or without isolation transformed into a salt or complex form of formula I.

5. The process according to claim 4, wherein the reaction is carried out in a solvent.

6. The process according to claim 5, wherein the reaction is carried out between 40° C. and the boiling point of the solvent.

7. The process according to claim 4, wherein the reaction is carried out in the presence of an organic base.

8. A method for imaging metal ions in a solution, biological samples, cell cultures, or body tissues, comprising achieving said imaging by the compound according to claim 1.

9. The method according to claim 8, wherein the imaging is carried out with a laser microscope.

10. A compound of formula I

I

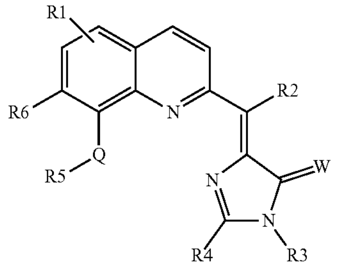

wherein

Q stands for —O—$R^5$ or —$NR^5R^9$ group,

W stands for an O atom, $R^1$, $R^2$, $R^3$ and $R^6$ stands for a H atom, $R^4$ stands for an —NH-aryl group, $R^5$, $R^9$, independently stand for a H atom or alkyl, or a carboxymethyl group, or $R^5$ and $R^6$ form a heterocyclic group, or $R^5$ and $R^9$ form a double bond connected to an alkyl group, or form a heterocyclic ring with $R^6$ group, or a salt or complex thereof.

11. A metal complex, which is the compound according to claim 10 in a complex with a $Zn^{2+}$ ion.

12. A method for imaging metal ions in a solution, biological samples, cell cultures or body tissues, comprising achieving said imaging by the compound according to claim 10.

13. The method according to claim 12, wherein the imaging is carried out with a laser microscope.

14. A compound, which is one of the following compounds:

28

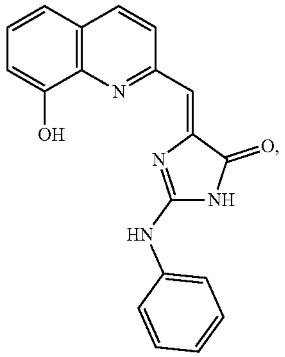

32

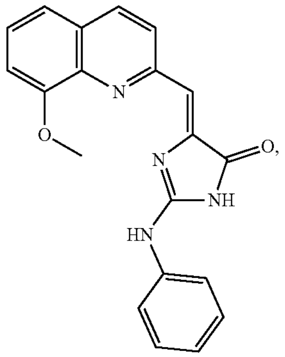

29

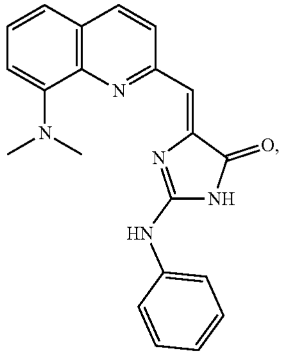

-continued

31

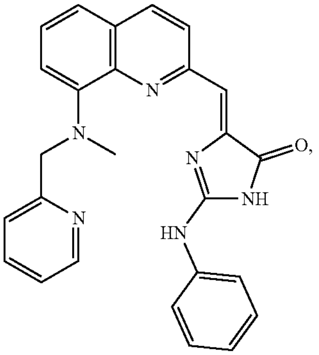

30

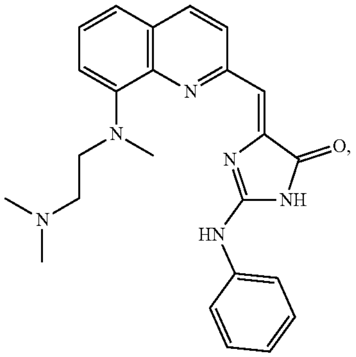

33

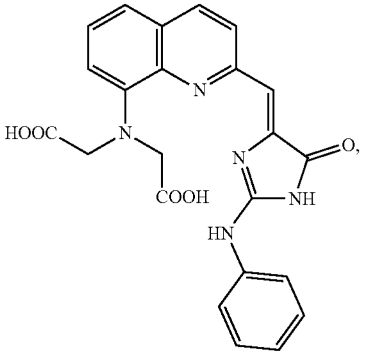

-continued

34

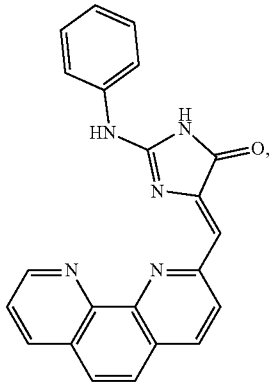

35

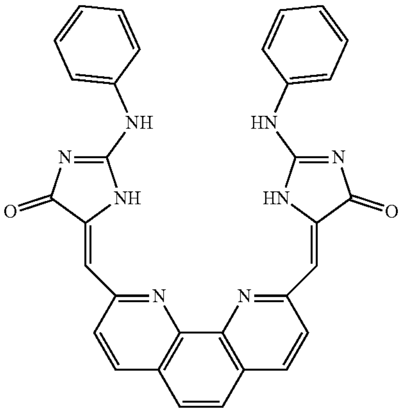

or a salt or complex thereof.

15. A metal complex, which is the compound according to claim 14 in a complex with a $Zn^{2+}$ ion.

16. A method for imaging metal ions in a solution, biological samples, cell cultures or body tissues, comprising achieving said imaging by the compound according to claim 14.

17. The method according to claim 16, wherein the imaging is carried out with a laser microscope.

* * * * *